United States Patent
Tang et al.

(10) Patent No.: US 9,120,762 B2
(45) Date of Patent: Sep. 1, 2015

(54) SALTS OF BICYCLO-SUBSTITUTED PYRAZOLON AZO DERIVATIVES, PREPARATION METHOD AND USE THEREOF

(71) Applicants: Jiangsu Hengrui Medicine Co., Ltd., Jiangsu (CN); Shanghai Hengrui Pharmaceutical Co., Ltd., Shanghai (CN)

(72) Inventors: Peng Cho Tang, Shanghai (CN); Hejun Lü, Shanghai (CN); Hongbo Fei, Shanghai (CN); Yiqian Chen, Shanghai (CN)

(73) Assignees: Jiangsu Hengrui Medicine Co., Ltd. (CN); Shanghai Hengrui Pharmaceutical Co., Ltd. (CN)

( * ) Notice: Subject to any disclaimer, the term of this patent is extended or adjusted under 35 U.S.C. 154(b) by 0 days.

(21) Appl. No.: 14/164,834

(22) Filed: Jan. 27, 2014

(65) Prior Publication Data
US 2014/0140953 A1 May 22, 2014

Related U.S. Application Data

(62) Division of application No. 13/377,342, filed as application No. PCT/CN2012/000760 on May 28, 2010, now Pat. No. 8,642,637.

(30) Foreign Application Priority Data

Jun. 11, 2009 (CN) .......................... 2009 1 0052946

(51) Int. Cl.
| | | |
|---|---|---|
| A61K 31/4152 | (2006.01) | |
| C07D 231/08 | (2006.01) | |
| C07D 231/46 | (2006.01) | |
| C07D 405/12 | (2006.01) | |
| C07D 409/12 | (2006.01) | |
| A61K 31/4155 | (2006.01) | |
| A61K 45/06 | (2006.01) | |
| C07C 211/05 | (2006.01) | |
| C07C 211/27 | (2006.01) | |
| C07C 215/08 | (2006.01) | |
| C07C 215/10 | (2006.01) | |
| C07C 215/40 | (2006.01) | |

(Continued)

(52) U.S. Cl.
CPC .......... *C07D 231/46* (2013.01); *A61K 31/4152* (2013.01); *A61K 31/4155* (2013.01); *A61K 45/06* (2013.01); *C07C 211/05* (2013.01); *C07C 211/27* (2013.01); *C07C 215/08* (2013.01); *C07C 215/10* (2013.01); *C07C 215/40* (2013.01); *C07C 279/14* (2013.01); *C07D 295/027* (2013.01); *C07D 405/12* (2013.01); *C07D 409/12* (2013.01)

(58) Field of Classification Search
CPC .......................... A61K 31/4152; C07D 231/08
USPC .......... 548/356.1, 364.1, 365.7; 514/403, 404
See application file for complete search history.

(56) References Cited

U.S. PATENT DOCUMENTS

| 7,452,874 B2 | 11/2008 | Duffy |
| 7,674,887 B2 | 3/2010 | Duffy et al. |
| 7,790,704 B2 | 9/2010 | Duffy et al. |

(Continued)

FOREIGN PATENT DOCUMENTS

| CN | 1444477 A | 9/2003 |
| CN | 101481352 A | 7/2009 |

(Continued)

OTHER PUBLICATIONS

"International Application No. PCT/CN2010/000760, International Preliminary Report dated Dec. 12, 2011", (w/ English Translation), 20 pgs.

(Continued)

*Primary Examiner* — Golam M M Shameem
(74) *Attorney, Agent, or Firm* — Schwegman Lundberg & Woessner, P.A.

(57) ABSTRACT

The pharmaceutically acceptable salts of bicycle-substituted pyrazolon azo derivatives represented by the general formula (I), their preparation methods, pharmaceutical compositions containing the same and their use as a therapeutic agent, especially as thrombopoietin (TPO) mimetics and their use as agonists of thrombopoietin receptor. The definitions of substituents in the general formula (I) are the same as the description.

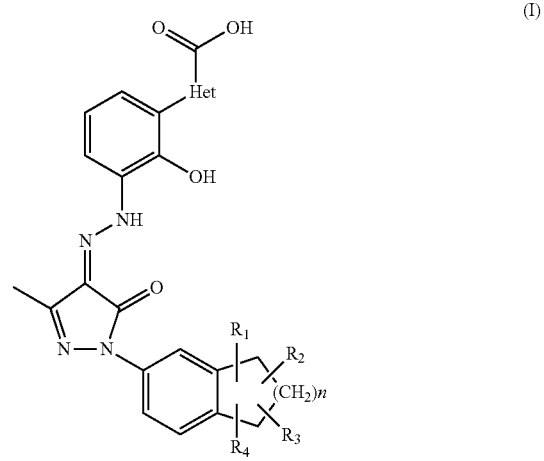

(I)

8 Claims, No Drawings

(51) Int. Cl.
*C07C 279/14* (2006.01)
*C07D 295/027* (2006.01)

(56) References Cited

U.S. PATENT DOCUMENTS

| 8,367,710 | B2 | 2/2013 | Tang et al. | |
|---|---|---|---|---|
| 8,642,637 | B2* | 2/2014 | Tang et al. | 514/404 |
| 2012/0164102 | A1 | 6/2012 | Tang et al. | |
| 2013/0123507 | A1 | 5/2013 | Tang et al. | |

FOREIGN PATENT DOCUMENTS

| WO | WO-0028987 | A1 | 5/2000 |
|---|---|---|---|
| WO | WO-0035446 | A1 | 6/2000 |
| WO | WO-0107423 | A1 | 2/2001 |
| WO | WO-0117349 | A1 | 3/2001 |
| WO | WO-0134585 | A1 | 5/2001 |
| WO | WO-0139773 | A1 | 6/2001 |
| WO | WO-0153267 | A1 | 7/2001 |
| WO | WO-0189457 | A2 | 11/2001 |
| WO | WO-03098992 | A2 | 12/2003 |
| WO | WO-2005066115 | A2 | 7/2005 |
| WO | WO-2009/092276 | A1 | 7/2009 |
| WO | WO-2010/142137 | A1 | 12/2010 |

OTHER PUBLICATIONS

"International Application No. PCT/CN2010/000760, Written Opinion mailed Sep. 2, 2010", (w/ English Translation), 18 pgs.
"U.S. Appl. No. 13/377,342, Response filed Aug. 13, 2013 to Non Final Office Action mailed May 13, 2013", 10 pgs.
"U.S. Appl. No. 13/377,342, Non Final Office Action mailed May 13, 2013", 9 pgs.
"U.S. Appl. No. 13/377,342, Notice of Allowance mailed Sep. 26, 2013", 11 pgs.
"U.S. Appl. No. 13/377,342, Response Filed Mar. 27, 2013 to Restriction Requirement mailed Feb. 6, 2013", 9 pgs.
"U.S. Appl. No. 13/377,342, Restriction Requirement mailed Feb. 6, 2013", 8 pgs.
"U.S. Appl. No. 13/377,342, Response Filed Aug. 13, 2013 to Non Final Office Action mailed May 13, 2013", 11 pgs.
"International Application No. PCT/CN2010/000760, International Search Report mailed Sep. 2, 2010", 10 pgs.
Bartley, T. D, et al., "Identification and cloning of a megakaryocyte growth and development factor that is a ligand for the cytokine receptor Mpl", Cell, 77(7), (1994), 1117-1124.
De Sauvage, Frederic J, et al., "Stimulation of megakaryocytopoiesis and thrombopoiesis by the c-Mpl ligand", Nature, 369(6481), (Jun. 16, 1994), 533-8.
Kaushansky, Kenneth, et al., "Promotion of megakaryocyte progenitor expansion and differentiation by the c-Mpl ligand thrombopoietin", Nature, 369(6481), (Jun. 16, 1994), 568-71.
Kuter, David J., et al., "The purification of megapoietin: a physiological regulator of megakaryocyte growth and platelet production", Proc Natl Acad Sci U S A., 91(23), (Nov. 8, 1994), 11104-8.
Kuter, David J., "Thrombopoietin: Biology and Clinical Applications", Oncologist, 1(1 & 2), (1996), 98-106.
Metcalf, Donald, "Blood. Thrombopoietin—at last.", Nature, 369(6481), (Jun. 16, 1994), 519-20.
Vigon, Isabelle, et al., "Molecular cloning and characterization of MPL, the human homolog of the v-mpl oncogene: identification of a member of the hematopoietic growth factor receptor superfamily", Proc Natl Acad Sci U S A., 89(12), (Jun. 15, 1992), 5640-4.
Wendling, Francoise, et al., "cMpl ligand is a humoral regulator of megakaryocytopoiesis", Nature, 369(6481), (Jun. 16, 1994), 571-4.
Wendling, Francoise, et al., "Mpl ligand or thrombopoietin: biological activities", Biotherapy,10(4), (1998), 269-77.

\* cited by examiner

US 9,120,762 B2

SALTS OF BICYCLO-SUBSTITUTED PYRAZOLON AZO DERIVATIVES, PREPARATION METHOD AND USE THEREOF

PRIORITY CLAIM TO RELATED APPLICATIONS

This application is a divisional of and claims the benefit of priority to U.S. application Ser. No. 13/377,342, filed Dec. 9, 2011, which is a national stage application under 35 U.S.C. §371 of PCT/CN2010/000760, filed May 28, 2010, and published as WO 2010/142137 A1 on Dec. 16, 2010, which claims priority to Chinese Application No. 200910052946.1, filed Jun. 11, 2009, which applications and publication are incorporated herein by reference and made a part hereof in their entirety, and the benefit of priority of each of which is claimed herein.

FIELD

This disclosure relates to pharmaceutical acceptable salts of novel bicyclo-substituted pyrazolon-azo derivatives, methods for their preparation, pharmaceutical compositions containing the same, and their use as a therapeutic agent, particularly as thrombopoietin (TPO) mimetics and agonists of the thrombopoietin receptor.

BACKGROUND

Thrombopoietin (TPO), also called megakaryocyte growth and development factor (MGDF), thrombocytopoiesis stimulating factor (TSF), c-myeloproliferative leukemia ligand (c-Mpl), mpl ligand, or megapoietin, is a glycoprotein that has been reported to regulate the production of platelets. See Wendling, F., et. al., *Biotherapy* 10(4): 269-77 (1998); Kuter D. J. et al., *The Oncologist*, 1: 98-106 (1996); Metcalf, *Nature* 369: 519-520 (1994).

Under certain circumstances, the activity of TPO results from the binding of TPO with the TPO receptor (also called Mpl). The TPO receptor has been cloned and its amino acid sequence has been described. See Vigon et al., *Proc. Nat. Acad. Sci.*, 89: 5640-5644 (1992).

TPO is a 332-amino acid glycosylated polypeptide that plays a key role in the regulation of megakaryocytopoiesis, and in the process in which platelets are produced by bone marrow megakaryocytes. See Kuter et al., *Proc. Nat. Acad. Sci. USA* 91: 11104-11108 (1994); Barley et al., *Cell* 77:1117-1124 (1994); Kaushansky et al., *Nature* 369:568-571 (1994); Wendling et al., *Nature* 369: 571-574 (1994); and Sauvage et al., *Nature* 369: 533-538 (1994). TPO is produced in the liver but functions mainly in the bone marrow, where it stimulates the differentiation of stem cells into megakaryocyte progenitors, and stimulates megakaryocyte proliferation, polyploidization and, ultimately, enters the platelet circulation in the body. TPO is also a primary regulator in situations involving thrombocytopenia and in a number of studies that include increasing platelet counts, platelet size and isotope incorporation into platelets of recipient animals. See, Metcalf *Nature* 369: 519-520 (1994). Specifically, TPO is considered to affect megakaryocytopoiesis by several ways: (1) it causes increase in size and number of megakaryocyte; (2) it increases DNA contents, the forms of polyploidy, and the number of megakaryocytes; (3) it increases megakaryocyte endomitosis; (4) it increases the number of mature megakaryocytes; (5) it increases the percentage of precursor cells, the number of small acetylcholinesterase positive cells, the number of bone marrow cells.

Platelets are necessary for blood clotting. When platelet counts are very low, a patient is at risk of death from catastrophic hemorrhage. Thus, TPO has been used for both the diagnosis and the treatment of various hematological disorders, for example, diseases primarily caused by platelet defects. Likewise, TPO may be useful for the treatment of thrombocytopenic conditions, especially those derived from chemotherapy, radiation therapy, or bone marrow transplantation for the treatment of cancer or lymphoma.

The slow recovery of platelet levels in patients suffering from thrombocytopenia is a serious problem, it is desirable to provide a compound for the treatment of thrombocytopenia by acting as a TPO mimetic. These peptides were designed to bind and activate the TPO receptor (TPO-R) but have no sequence homology to the natural TPO. In recent years, a number of active small-molecule TPO mimetics have been reported, including cyclic polyamine derivatives (WO00/28987), thiazol-2-yl-benzamides (WO01/07423, WO01/53267), azo-aryl derivatives (WO00/35446, WO01/17349), 2-aryl-naphthimidazoles (WO01/39773, WO01/53267), and semicarbazone derivatives (WO01/34585). In cell-based systems, all of these molecules can activate signal transduction pathways that are dependent on the presence of the TPO receptor on the cell membrane. Certain types of compounds can directly act on the TPO receptor itself. Some of the most preferred compounds of this series were found to stimulate the proliferation and differentiation of TPO-responsive human cell lines and TPO in human bone marrow cultures that has a concentration below 100 nM.

Several patents assigned to GlaxoSmithKline described a thrombopoietin analog, eltrombopag (WO-2003098992/WO-01089457), with good activity.

The present disclosure provides a series of pharmaceutical acceptable salts of bicyclo-substituted pyrazolon-azo derivatives, which are more effective TPO mimetics and TPO receptor agonists.

The international application no. PCT/CN2009/000001 submitted by the applicant of the present invention on 4 Jan. 2009 described a novel bicyclo-substituted pyrazolon-azo derivatives and their use as thrombopoietin (TPO) mimetics and agonists of the thrombopoietin receptor. Six examples (Example 1, Example 9, Example 15, Example 28, Example 43 and Example 52) described in the international application provided the compounds respectively as follows: 2'-hydroxy-3'-[N'-(1-indan-5-yl-3-methyl-5-oxo-1,5-dihydro-pyrazol-4-ylidene)-hydrazino]-biphenyl-3-carboxylic acid, 5-{2-hydroxy-3-[N'-(1-indan-5-yl-3-methyl-5-oxo-1,5-dihydro-pyrazol-4-ylidene)-hydrazino}-phenyl]-furan-2-carboxylic acid, 5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid, 4-(2-hydroxy-3-[N'-(3-methyl-5-oxo-1-(5,6,7,8-tetrahydro-naphthalen-2-yl)-1,5-dihydro-pyrazol-4-ylidene)-hydrazino]biphenyl-furan-2-carboxylic acid, 5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid, 4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid, and the esters thereof. These compounds were tested to show good activity as TPO receptor agonists. Therefore this international application was whole incorporated here by reference. However, the international application no. PCT/CN2009/000001 didn't describe the pharmaceutical acceptable salts of the compounds.

The inventor of the disclosure discovered that the free acid form of bicyclo-substituted pyrazolon-azo derivatives were poorly soluble in conventional solvents, and thus disadvantageous to be prepared into a medicinal dosage form, limiting their in vivo bioavailability. It is necessary to develop new forms of bicyclo-substituted pyrazolon-azo derivatives to improve their solubility and pharmacokinetic absorption, which can be used in conventional preparation of dosage forms.

SUMMARY

In order to overcome the insufficiency of the prior art, the present invention provides pharmaceutically acceptable salts of novel bicyclo-substituted pyrazolon-azo derivatives, methods for their preparation, pharmaceutical compositions containing the same, and their use as a therapeutic agent, particularly as thrombopoietin (TPO) mimetics and agonists of the thrombopoietin receptor. The salts have good activities for treating thrombocytopenia, improved solubility, good in vivo activities, better bioavailability, lower toxicity and being a good candidate in the preparation of a medicament for the treatment of thrombocytopenia.

"The compounds of the present disclosure" and "the salts of the present disclosure" are interchangeable, both of which are the pharmaceutically acceptable salts of bicyclo-substituted pyrazolon-azo derivatives represented by formula (I).

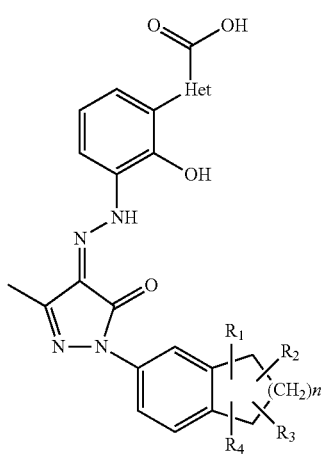

wherein:

Het is selected from the group consisting of phenyl, furyl and thienyl;

$R_1$, $R_2$, $R_3$ and $R_4$ are each independently selected from the group consisting of hydrogen and alkyl;

n is 0, 1 or 2;

the salts are base addition salts.

Furthermore, the present disclosure relates to salts of the compounds having formula (IA).

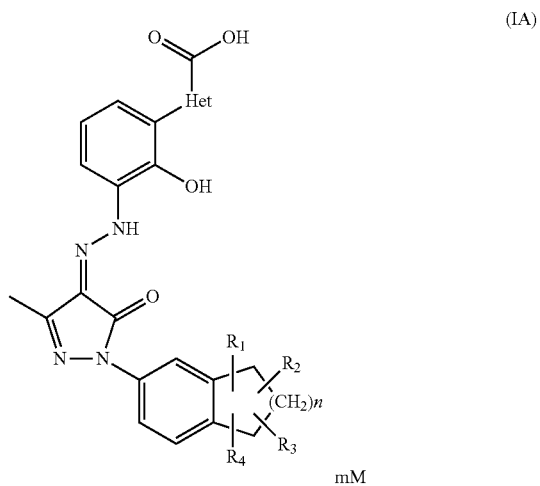

wherein:

Het is selected from the group consisting of phenyl, furyl and thienyl;

$R_1$, $R_2$, $R_3$ and $R_4$ are each independently selected from the group consisting of hydrogen and alkyl;

M is selected from the group consisting of metal ion, ammonium ion and basic amino acid;

m is 1 or 2;

n is 0, 1 or 2;

the salts are base addition salts.

The term "free acid" refers to bicyclo-substituted pyrazolon-azo derivatives having formula (I).

The equivalent refers to those tautomers of the compounds having formula (I), which is well known by the person skilled in the art. The tautomers of the compounds having formula (I) include the following formula (II) and formula (III), but not limited to:

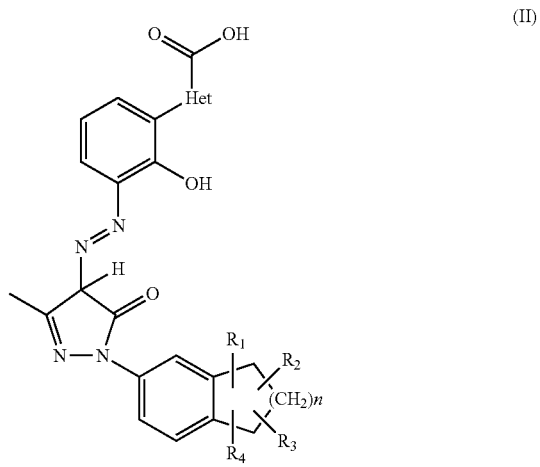

-continued

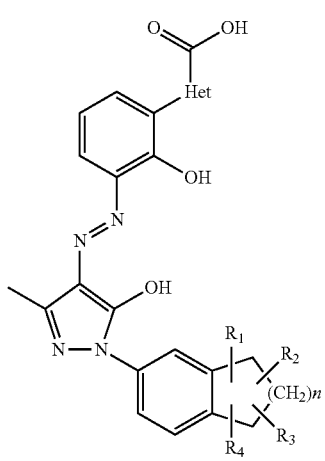
(III)

All tautomers of the compounds having formula (I) are included in the scope of the present disclosure and all of them are included in the definition of the compounds having formula (I).

The term "pharmaceutically acceptable salt" in present disclosure refers to pharmaceutically nontoxic base addition salts. The salts are those formed between the compounds having formula (I) and appropriate bases such as alkali metal hydroxid, basic amino acid, amine or quaternary ammonium, including sodium salt, lithium salt, potassium salt, calcium salt, magnesium salt, arginine salt, lysine salt, methanamine salt, dimethylamine salt, trimethylamine salt, ethylamine salt, diethylamine salt, triethylamine salt, ethanolamine salt, piperazine salt, dibenzyl ethylenediamin salt, meglumine salt, tromethamine salt, tetramethyl quaternary ammonium salt, tetraethyl quaternary ammonium salt and choline salt, preferably diethylamine salt, ethanolamine salt, choline salt, piperazine salt, meglumine salt and tromethamine salt, more preferably ethanolamine salt, choline salt, meglumine salt and tromethamine salt, and the most preferably ethanolamine salt.

The pharmaceutically acceptable salts of the compounds having formula (I) of the present disclosure preferably include, but are not limited to:

| Example No. | Structure | Name |
|---|---|---|
| 1 | 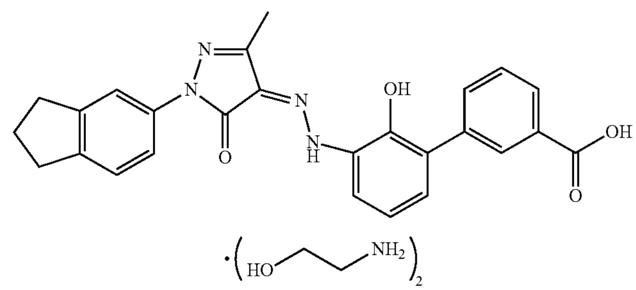 | (Z)-2'-hydroxy-3'-[N'-(1-indan-5-yl-3-methyl-5-oxo-1,5-dihydro-pyrazol-4-ylidene)-hydrazino]-biphenyl-3-carboxylic acid bis-(ethanolamine) |
| 2 | 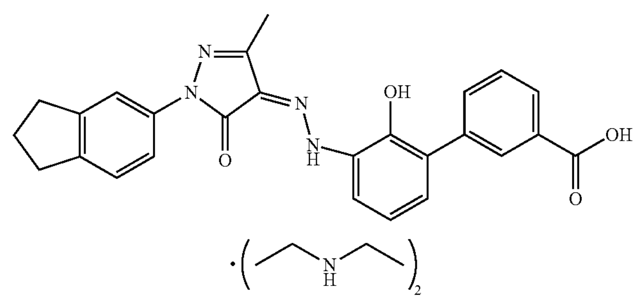 | (Z)-2'-hydroxy-3'-[N'-(1-indan-5-yl-3-methyl-5-oxo-1,5-dihydro-pyrazol-4-ylidene)-hydrazino]-biphenyl-3-carboxylic acid bis-(diethylamine) |
| 3 | 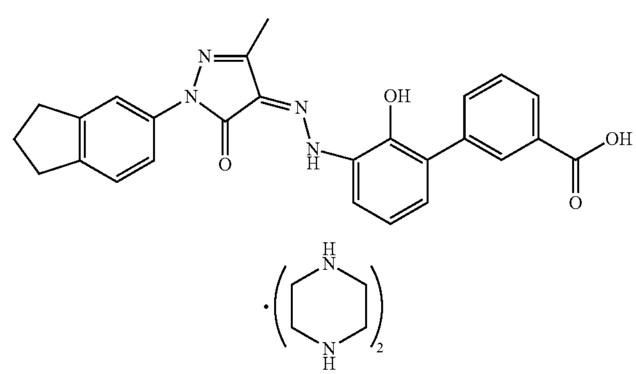 | (Z)-2'-hydroxy-3'-[N'-(1-indan-5-yl-3-methyl-5-oxo-1,5-dihydro-pyrazol-4-ylidene)-hydrazino]-biphenyl-3-carboxylic acid bis-(piperazine) |

| Example No. | Structure | Name |
|---|---|---|
| 4 | 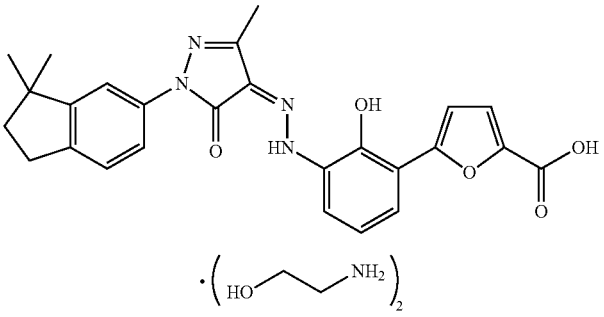 | (Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid bis-(ethanolamine) |
| 5 | 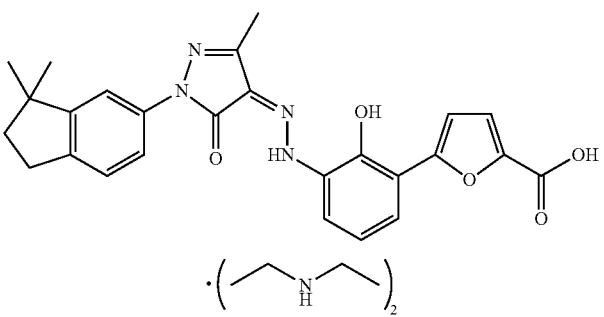 | (Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid bis-(diethylamine) |
| 6 | 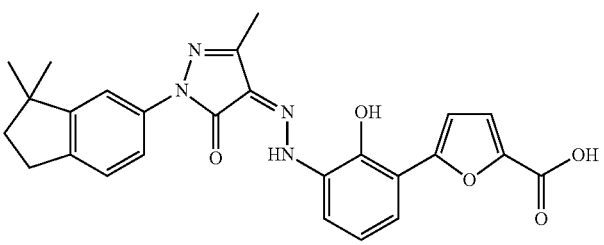 | (Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid bis-(piperazine) |
| 7 | 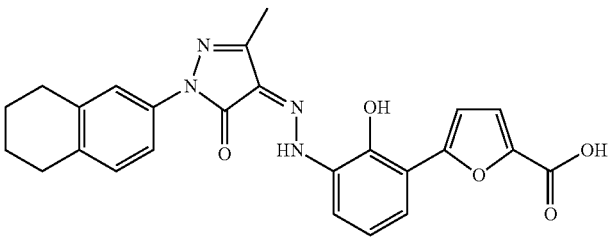 | (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(ethanolamine) |

| Example No. | Structure | Name |
|---|---|---|
| 8 | 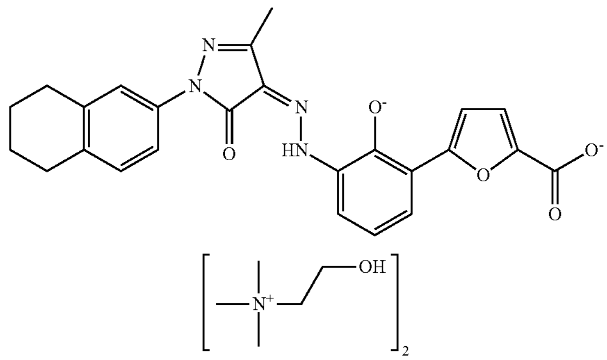 | (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(choline) |
| 9 | 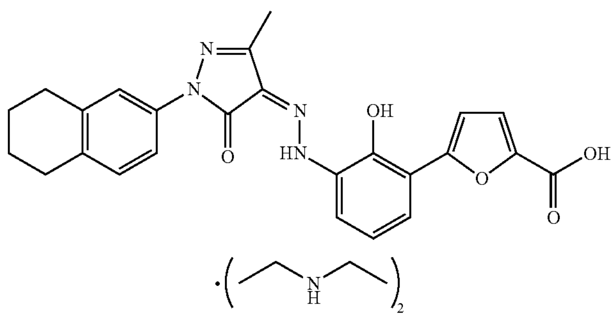 | (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(diethylamine) |
| 10 | 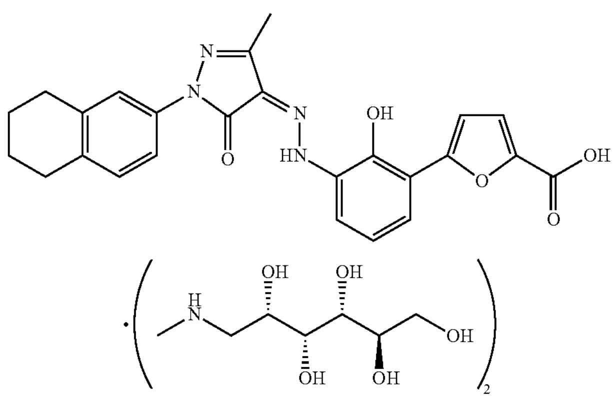 | (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(meglumine) |
| 11 | 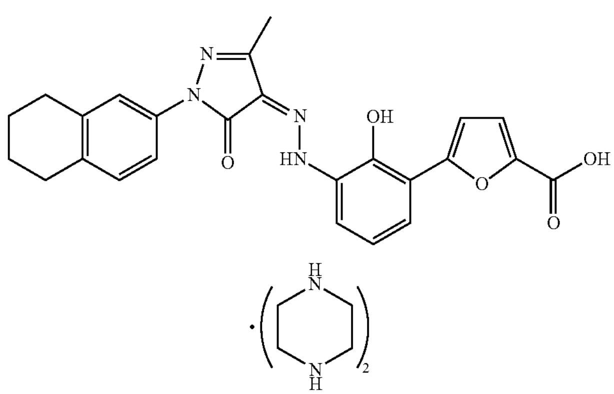 | (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(piperazine) |

| Example No. | Structure | Name |
|---|---|---|
| 12 | 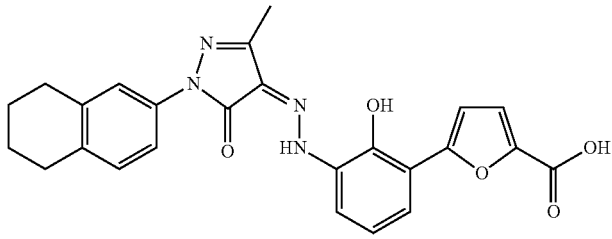 | (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(trometamol) |
| 13 | 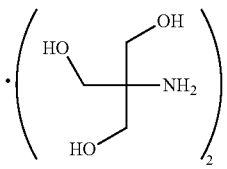 | (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(dibenzylethylenediamine) |
| 14 | 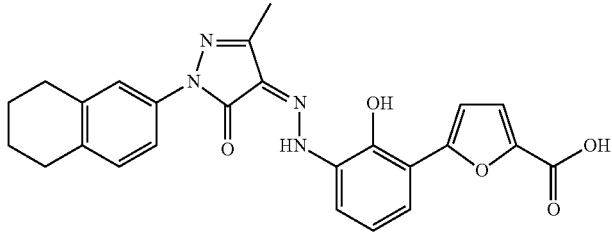 | (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid disodium salt |
| 15 | 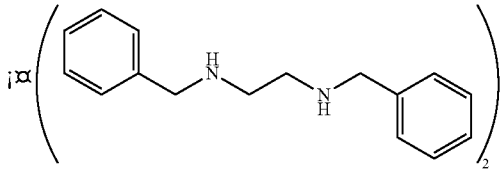 | (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(L-arginine) |

-continued

| Example No. | Structure | Name |
|---|---|---|
| 16 | 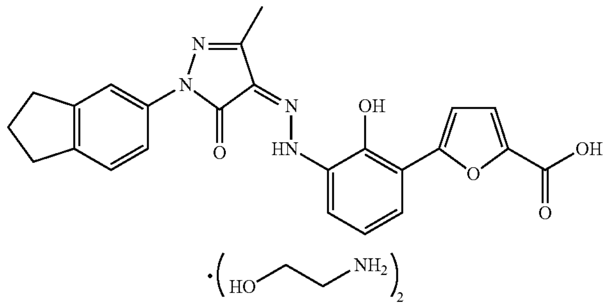 | (Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid bis-(ethanolamine) |
| 17 | 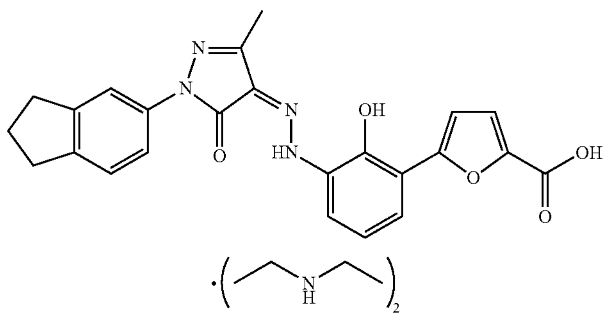 | (Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid bis-(diethylamine) |
| 18 | 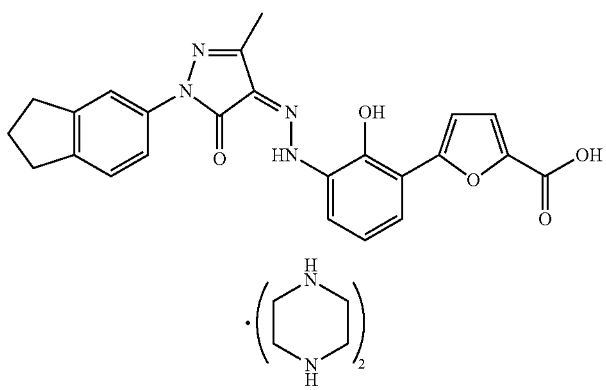 | (Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid bis-(piperazine) |
| 19 | 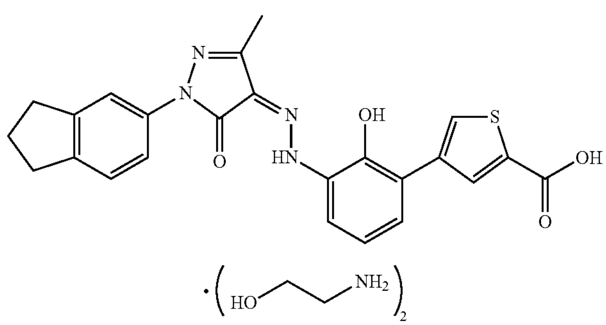 | (Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid bis-(ethanolamine) |

| Example No. | Structure | Name |
|---|---|---|
| 20 | 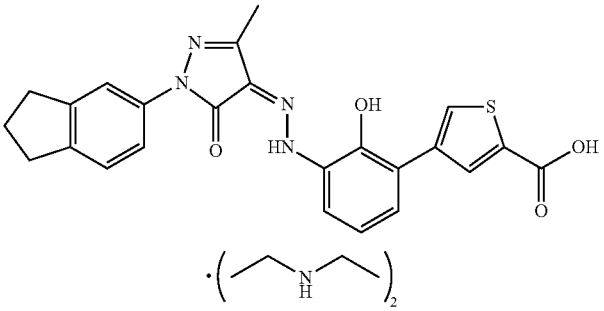 | (Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid bis-(diethylamine) |
| 21 | 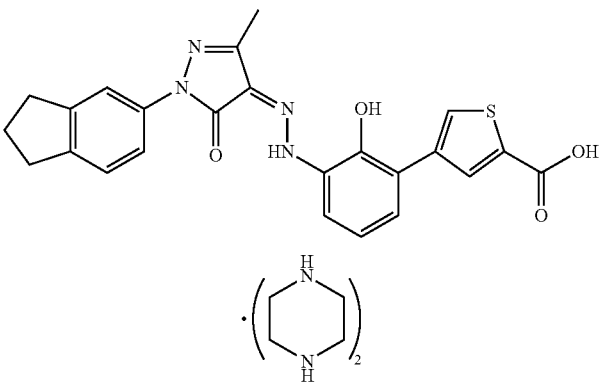 | (Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid bis-(piperazine) |
| 22 | 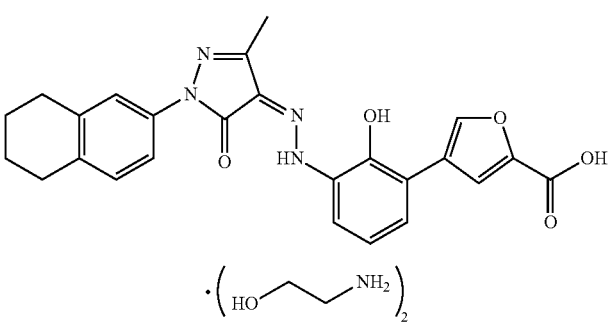 | (Z)-4-(2-Hydroxy-3-{N'-[3-methyl-5-oxo-1-(5,6,7,8-tetrahydro-naphthal-2-yl)-1,5-dihydro-pyrazol-4-ylidene]-hydrazino}-phenyl)-furan-2-carboxylic acid bis-(ethanolamine) |
| 23 | 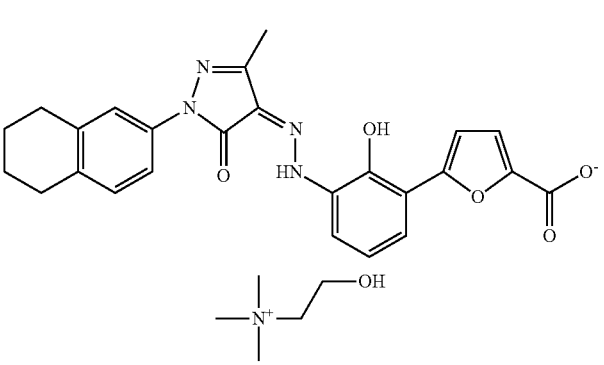 | (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid choline |

The present disclosure relates to a process for preparing the pharmaceutically acceptable salts of compounds having formula (I), comprising the steps of:
(a) dissolving or suspending the free acid of the present disclosure (the compound having formula (I)) in an organic solvent, wherein the organic solvent is selected from the group consisting of methanol, ethanol, acetone, ethyl acetate and tetrahydrofuran, preferably tetrahydrofuran;
(b) adding a base to the mixture with stirring, wherein the base may be organic or inorganic base such as alkali metal hydroxid or alkali earth metal hydroxid, basic amino acid, amine or quaternary ammonium;
(c) obtaining the pharmaceutically acceptable salts of the compound having formula (I), wherein the inorganic bases include alkaline metal hydroxides which are selected from the group consisting of the sodium hydroxide, lithium hydroxide, potassium hydroxide, calcium hydroxide, magnesium hydroxide; the basic amino acids are selected from the group consisting of lysine and arginine; the amines are selected from the group consisting of methanamine, dimethylamine, trimethylamine, ethylamine, diethylamine, triethylamine, ethanolamine, piperazine, dibenzyl ethylenediamin, meglumine and tromethamine; and the quaternary ammoniums are selected from the group consisting of tetramethyl quaternary ammonium, tetraethyl quaternary ammonium, choline hydroxide, preferably diethylamine, ethanolamine, choline hydroxide, piperazine, meglumine and tromethamine, more preferably ethanolamine, choline hydroxide, meglumine and tromethamine, the most preferably ethanolamine In step (b), the equivalence ratio of free acid and alkaline metal hydroxide, basic amino acid, amine and quaternary ammonium was preferably 1:5~5:1, more preferably 1:1~1:3 and the most preferably 1:1~1:2.

In step (c), the separation of salts preferably included direct filtration from the reaction mixture, concentration from the reaction mixture and recrystallization from an organic solvent. The salts can be dried in the condition such as vacuum drying or high temperature air drying.

The reactions of salt formation are generally undertaken in the conditions of cooling, room temperature or heating. However, it was worth noting that the reaction temperature is related to the salt formation, which is well known by the person skilled in the art. The range of the reaction temperatures of the present disclosure is from room temperature to the boiling point of the reaction solvent, preferably 0~40° C. The person skilled in the art can easily determine the most preferably reaction temperature of salt forming reactions by conventional techniques.

The present disclosure relates to use of the pharmaceutically acceptable salts of the compounds having formula (I) in the preparation of a thrombopoietin receptor agonist.

The present disclosure relates to use of the pharmaceutically acceptable salts of the compounds having formula (I) in the preparation of a medicament for the treatment of thrombocytopenia, wherein the medicament is co-administered with a drug selected from the group consisting of a colony stimulating factor, a cytokine, a chemokine, an interleukin or cytokine receptor agonist or antagonist, a soluble receptor, a receptor agonist or antagonist antibody, or one or more peptides or small molecule compounds that have the same mechanism with the drug.

The present disclosure relates to the pharmaceutically acceptable salts of the compounds having formula (I), for use as a medicament for the treatment of thrombocytopenia, wherein the medicament is co-administered with a drug selected from the group consisting of a colony stimulating factor, a cytokine, a chemokine, an interleukin or cytokine receptor agonist or antagonist, a soluble receptor, a receptor agonist or antagonist antibody, or one or more peptides or small molecule compounds that have the same mechanism with the drug, wherein the medicament is in the form of oral dosage form, or the medicament is in the form of parenteral dosage form.

The present disclosure relates to a method for the treatment of thrombocytopenia comprising a step of administering to a subject in need thereof a therapeutically effective amount of the pharmaceutically acceptable salts of the compounds having formula (I), wherein the pharmaceutically acceptable salt is co-administered with a drug selected from the group consisting of a colony stimulating factor, a cytokine, a chemokine, an interleukin or cytokine receptor agonist or antagonist, a soluble receptor, a receptor agonist or antagonist antibody, or one or more peptides or small molecule compounds that have the same mechanism with the drug, wherein the pharmaceutically acceptable salt is in the form of oral dosage form, or the pharmaceutically acceptable salt is in the form of parenteral dosage form.

The present disclosure relates to pharmaceutical compositions comprising a therapeutically effective amount of the pharmaceutically acceptable salts of the compounds having formula (I) and pharmaceutically acceptable carriers or diluent agents, wherein the composition is co-administered with a drug selected from the group consisting of a colony stimulating factor, a cytokine, a chemokine, an interleukin and cytokine receptor agonist. The present disclosure also relates to use of the compositions in the preparation of a medicament for the treatment of thrombocytopenia, wherein the co-administration comprises using the drugs of the present disclosure at the same time or successively.

The present disclosure relates to a process of preparing the pharmaceutical compositions comprising a therapeutically effective amount of the pharmaceutically acceptable salts of the compounds having formula (I) and pharmaceutically acceptable carriers or diluent agents, wherein the process comprises the step of combining the compounds having formula (I) with pharmaceutically acceptable carriers or diluent agents.

In the preparation process of pharmaceutical compositions, it is important to prepare the drug into an appropriate form operated and dealt conveniently, which is not only in the view of commercial available preparation but also in the view of preparing the pharmaceutical dosage forms containing the active compounds.

In another aspect, it is important to offer a reliable, reproducible and constant drug plasma concentration curve after administrating to a subject in the preparation process of pharmaceutical compositions.

Other important factors include chemical durability, solid-state stability and storage life of the active ingredient. The drugs containing their composition can be preferably stored relatively for a long time with no obvious change in physical and chemical characters of their active components such as chemical composition, density, hygroscopicity and solubility.

It is also important to provide chemical pure drug as possible.

Typically, a drug can offer following advantages: convenient treating, preparing appropriate drug dosage forms and reliable solubility if the drug can be obtained in a stable form such as stable crystal form, which is well known by the person of skilled in the art.

Effective amount of the active ingredient in pharmaceutical dosage unit as described above will be nontoxic, preferably selected from the range 0.001~400 mg/kg of total weight, more preferably 0.001~50 mg/kg. When treating a subject in need of a TPO mimetics, the selected dose is administrated preferably orally or parenterally. Preferred parenteral forms include topical, rectal, transdermal administration forms, injection and continuous infusion. Oral dosage units for human administration preferably contain from 0.05 to 3500 mg of active ingredient, most preferably from 0.5 to 1000 mg of active ingredient. Oral administration, which uses lower dosage is preferred. Parenteral administration, at high dosages, however, also can be used when safe and convenient for the patient. The above dosages relates to the preferred amount of the active ingredient expressed as the free acid.

It will be understood by one skilled in the art that the optimal quantity and spacing of individual dosages of the active ingredient will depend on the nature and extent of the condition to be treated, the form, route and site of administration, and the particular patient to be treated, and that such optimums can be determined by conventional techniques. It will also be appreciated by one skilled in the art that the optimal course of treatment, i.e., the number of doses of the active ingredient given per day for a defined number of days, can be ascertained by those skilled in the art using conventional course of treatment determination tests.

The compounds of the present disclosure can be administrated orally or parenterally, wherein the compounds can be prepared into tablets, pills, powder and granules used in different routes of administration. In above solid dosage forms, the active components mixed with at least one kind of inert diluent. According to conventional operation, oral dosage forms also include other substance such as lubricants, glidants and antioxidants besides inert diluent. If made into capsules, tablets and pills, dosage forms contain buffering agents. Tablets and pills can be made into sustained-release dosage forms.

Although non-aqueous emulsions can be used, parenteral dosage forms of the present disclosure contain sterile aqueous solution and these dosage forms also contain adjuvants, for example antiseptics, wetting agents, penetrating agents, buffering agents, emulsifying agents and dispersants. The sterilizing process can use bacteria retaining filter and sterilizing agents are added to the compositions which were irradiated or heated to sterilize.

Compared to the free acids, the salts of the present disclosure have following advantages:
(1) The salts of the present disclosure are easily dissolved in the conventional solvents such as water, methanol, 0.1% hydrochloric acid and adapted to prepare conventional dosage forms, wherein the solubility of ethanolamine salts are improved obviously in 0.1% hydrochloric acid.
(2) The salts of the present disclosure have improved stability.
(3) The salts of the present disclosure have better biological activity in vitro.
(4) The salts of the present disclosure have better pharmacokinetics characters in vivo, better absorption, higher bioavailability and better pharmacokinetics curve, wherein ethanolamine salt, choline salt, piperazine salt, meglumine salt and tromethamine salt have better pharmacokinetics characters, preferably ethanolamine salt.
(5) The preparation process of the salts of the present disclosure has the advantages of high yield, high purity, quick, convenience and low cost, wherein ethanolamine salt, choline salt, diethylamine salt and piperazine salt are more advantageous in process routes, those of which can be crystallized directly.

Compared to the free acids, the salts of the present disclosure have better characters of solubility, stability, biological activity in vitro and pharmacokinetics, preferably diethylamine salt, ethanolamine salt, choline salt, piperazine salt, meglumine salt and tromethamine salt, more preferably ethanolamine salt, choline salt, meglumine salt and tromethamine salt, the most preferably ethanolamine salt.

DETAILED DESCRIPTION

Unless otherwise stated, the following terms used in the specification and claims have the meanings described below.

The term "ethanolamine" refers to "2-aminoethanol".

The term "choline" refers to "(2-hydroxyethyl)trimethylamine".

The term "meglumine" refers to "N-methyl-D-meglumine".

The term "pharmaceutical composition" refers to a mixture of one or more of the pharmaceutically acceptable salts of the compound described herein or prodrugs thereof, with other chemical components such as physiologically/pharmaceutically acceptable carriers. The purpose of a pharmaceutical composition is to facilitate administration of a compound to an organism.

The term "stability" refers to chemical stability and solid stability.

The term "chemical stability" refers to storage of the compounds of the present disclosure including isolated forms or dosage forms mixed with pharmaceutically acceptable carriers or diluents (for example oral dosage such as tablets, capsules and so on) in standard conditions with insignificant chemical degradation or chemical decomposition.

The term "solid stability" refers to storage of the compounds of the present disclosure including isolated solid forms or dosage forms mixed with pharmaceutically acceptable carriers or diluents in solid forms (for example oral dosage such as tablets, capsules and so on) in standard conditions with insignificant solid state transformation (for example crystallization, recrystallization, solid-state phase change, hydration, dehydration, solvation or solvent removal).

The examples of the term "stored in standard conditions" include the range of temperature from −80° C. to +50° C. (preferably from 0° C. to 40° C., more preferably at room temperature, such as 15° C.~30° C.), the range of pressure from 0.1 pa to 2 pa (preferably at atmosphere), the range of relative humidity from 5% to 95% (preferably 10%~60%) and/or exposed under 460 lux UV/visible light experiencing longer time (longer than or equal to six months).

The term "parenteral administration" includes intravenous, intramuscular, subcutaneous, intranasal, intrarectal, intravaginal or intraperitoneal administration, preferably oral administration.

The term pharmaceutical "hygroscopicity" refers to the character that the capability or degree of the substance can absorb water under certain temperature and humidity. The test samples are solid ingredients satisfied with Drug Quality Control Standard. The packages of the drugs and storage conditions can refer to the results of the above test.

Synthesis Method of the Disclosure Compound

In order to achieve the purpose of the disclosure, the disclosure applies the following technical solutions:

The synthesis method of the compound having formula (I) refers to the example 1, example 9, example 15, example 28, example 43 and example 52 of the international application no. PCT/CN2009/000001 submitted on Jan. 4, 2009. The application was whole incorporated herein by reference.

The process for preparing the pharmaceutically acceptable salts of the compounds having formula (I) comprises the steps of:

(a) dissolving or suspending the free acid of the present disclosure (the compound having formula (I)) in an organic solvent, wherein the organic solvent is selected from the group consisting of methanol, ethanol, acetone, ethyl acetate and tetrahydrofuran, preferably tetrahydrofuran;

(b) adding a base to the mixture with stirring, wherein the base may be organic or inorganic base such as alkali metal hydroxide or alkali earth metal hydroxide, basic amino acid, amine or quaternary ammonium;

(c) obtaining the pharmaceutically acceptable salt of the compound having formula (I), wherein the inorganic bases include alkaline metal hydroxides which are selected from the group consisting of the sodium hydroxide, lithium hydroxide, potassium hydroxide, calcium hydroxide, magnesium hydroxide; the amines and the quaternary ammoniums are selected from the group consisting of tetramethyl quaternary ammonium, tetraethyl quaternary, ethanolamine, choline, lysine, arginine, methanamine, dimethylamine, trimethylamine, ethylamine, diethylamine, triethylamine, dibenzyl ethylenediamin, meglumine, piperazine and tromethamine; preferably diethylamine, ethanolamine, piperazine, choline hydroxide, meglumine and tromethamine, more preferably ethanolamine, choline hydroxide, meglumine and tromethamine, the most preferably ethanolamine.

In step (b), the equivalence ratio of free acid and the base was preferably 1:5~5:1, more preferably 1:1~1:3 and the most preferably 1:1~1:2.

In step (c), the separation of salts preferably included direct filtration from the reaction mixture, the concentration from the reaction mixture and recrystallization from an organic solvent. The salts can be dried in the condition such as vacuum drying or high temperature air drying.

The reactions of salt formation above are generally undertaken in the condition of cooling, room temperature or heating. However, it was worth noting that the reaction temperature has influence on the salt forming reaction, which is well known by the person skilled in the art. The range of the reaction temperatures of the present disclosure is from room temperature to the boiling point of the reaction solvent, preferably 0-40° C. The person skilled in the art can easily determine the most preferably reaction temperature of salt forming reactions by conventional techniques.

The present disclosure is further described by the following Examples which are not intended to limit the scope of the disclosure.

EXAMPLES

The structures of all compounds were identified by nuclear magnetic resonance ($^1$H NMR) or mass spectrometry (MS).

NMR was performed on a Bruker AVANCE-400 spectrometer. The appropriate solvents included deuterated-methanol ($CD_3OD$), deuterated-chloroform ($CDCl_3$) and deuterated-dimethyl sulfoxide ($DMSO-d_6$) with tetramethylsilane (TMS) as the internal standard and chemical shifts were recorded as ppm ($10^{-6}$).

MS was determined on a FINNIGAN LCQ Ad (ESI) mass spectrometer (Thermo, Model: Finnigan LCQ advantage MAX).

$EC_{50}$ was determined on a NovoStar ELIASA (BMG Co. German).

The thin-layer silica gel refers to Yantai Huanghai HSGF254 or Qingdao GF254 silica gel plate. The dimension of the plates used in TLC was 0.15 mm~0.2 mm, and the dimension of the plates used in product purification was 0.4 mm~0.5 mm Column chromatography generally used Yantai Huanghai 200~300 mesh silica gel as carrier.

HPLC was determined on an Agilent 1200DAD high pressure liquid chromatography spectrometer (Sunfire C18 150× 4.6 mm chromatographic column) and a Waters 2695-2996 high pressure liquid chromatography spectrometer (Gimini C18 150×4.6 mm chromatographic column).

Pressured hydrogenation reactions were performed with a Parr 3916EKX hydrogenation spectrometer and a QL hydrogen generator. Microwave reactions were performed with a CEM Discover-S 908860 microwave reactor.

In hydrogenation reactions, the reaction system was generally vacuumed and filled with hydrogen, repeat the operation three times.

The known starting material of the invention can be prepared by the conventional synthesis method in the art, or be purchased from ABCR GmbH & Co. KG, Acros Organics, Aldrich Chemical Company, Accela ChemBio Inc or Dari chemical Company, etc.

Unless otherwise stated, the following reactions were placed under nitrogen atmosphere.

The term "nitrogen atmosphere" refers to that a reaction flask is equipped with a 1 L nitrogen balloon.

The term "hydrogen atmosphere" refers to that a reaction flask is equipped with a 1 L hydrogen balloon.

Unless otherwise stated, the solution used in following reaction refers to an aqueous solution.

The term "TLC" refers to thin layer chromatography.

The term "HPLC" refers to high performance liquid chromatogram.

HPLC test conditions: run time: 30 min, column temperature: 30° C. PDA: 230 nm, mobile phase: acetonitrile:water (0.1% trifluoroacetic acid)=25:75, flow rate: 1.0 mL/minute.

Chromatographic column: C18, 150*4.6 mm Gemini

Example 1

(Z)-2'-hydroxy-3'-[N'-(1-indan-5-yl-3-methyl-5-oxo-1,5-dihydro-pyrazol-4-ylidene)-hydrazino]-biphenyl-3-carboxylic acid bis-(ethanolamine)

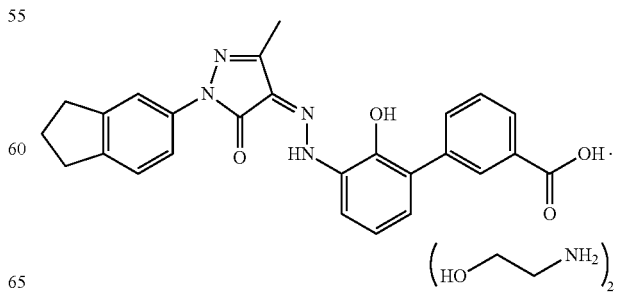

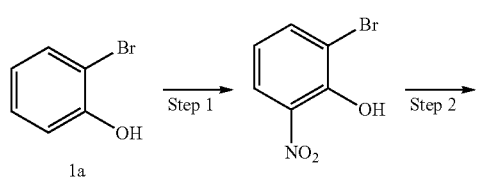
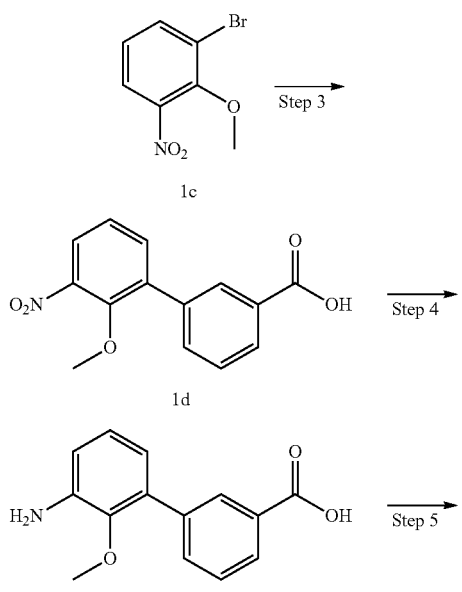
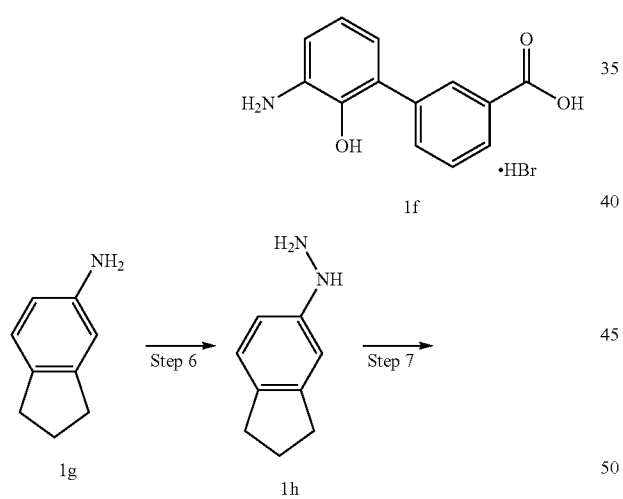
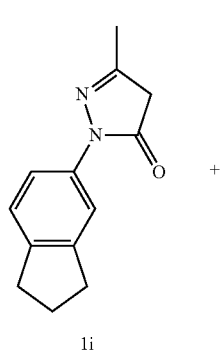
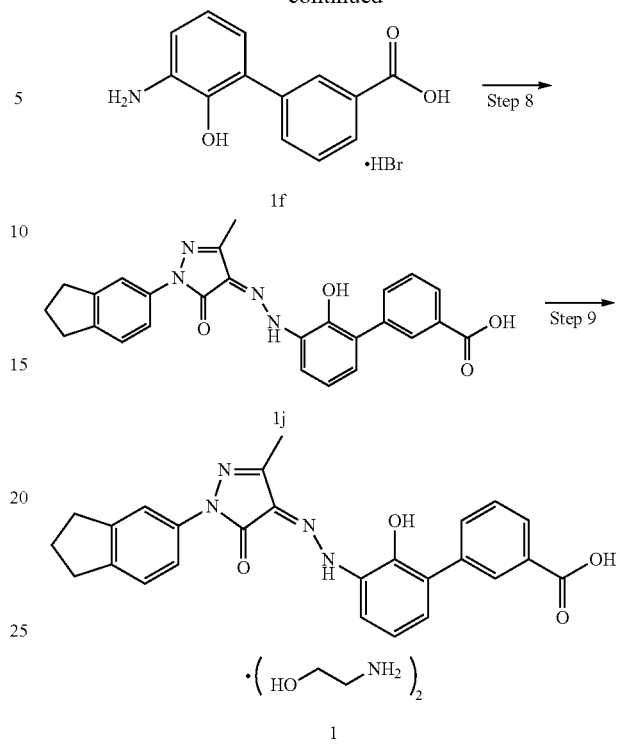

Step 1

2-Bromo-6-nitro-phenol

A solution of 60 mL of concentrated sulfuric acid diluted with 186 mL of water was cooled to room temperature. Sodium nitrate (79.2 g, 0.93 mol) was added to the solution. 2-Bromo-phenol 1a (60 mL, 0.52 mol) was added dropwise at such a rate that the reaction temperature was kept below 25° C. The reaction mixture was stirred at room temperature for 2 hours. The precipitate was dissolved in 320 mL of ethyl acetate. The mixture was washed with water and saturated brine, dried over anhydrous magnesium sulfate, filtered and the filtrate was concentrated under reduced pressure. The resulting residue was purified by silica gel column chromatography to obtain the title compound 2-bromo-6-nitro-phenol 1b (48.2 g, yield 42.8%) as a yellow solid.

MS m/z (ESI): 218 [M+1]

$^1$H NMR (400 MHz, CDCl$_3$): δ 11.18 (s, 1H), 8.12-8.15 (m, 1H), 7.89-7.91 (m, 1H), 6.88-7.02 (m, 1H)

Step 2

1-Bromo-2-methoxy-3-nitro-benzene

2-Bromo-6-nitro-phenol 1b (46.55 g, 0.214 mol) was dissolved in 500 mL of acetone followed by addition of potassium carbonate (35.36 g, 0.26 mol) and iodomethane (20.1 mL, 0.32 mol). The reaction mixture was heated to reflux at 70° C. for 40 hours. The reaction mixture was concentrated under reduced pressure and diluted with 1300 mL of ethyl acetate and 500 mL of water. The aqueous layer was extracted with ethyl acetate (300 mL×2). The combined organic extracts were washed with 4 M hydrochloric acid and saturated sodium bicarbonate solution and then dried over anhydrous magnesium sulfate, filtered and the filtrate was concentrated under reduced pressure. The resulting residue was purified by silica gel column chromatography to obtain the title compound 1-bromo-2-methoxy-3-nitro-benzene 1e (44.59 g, yield 90.0%) as a brown solid.

MS m/z (ESI): 234 [M+1]

Step 3

2'-Methoxy-3'-nitro-biphenyl-3-carboxylic acid

1-Bromo-2-methoxy-3-nitro-benzene 1c (23.25 g, 0.10 mol), 3-carboxyphenylboronic acid (19.5 g, 117 mmol) and tetrakis(triphenylphosphine)palladium (8.86 g, 7.7 mol) were dissolved in a solvent mixture of 100 mL of 2 M sodium carbonate solution and 500 mL of 1,4-dioxane. The reaction mixture was heated to reflux at 105° C. for 43 hours. The mixture was concentrated under reduced pressure and then 300 mL of 6 N hydrochloric acid and 400 mL of ethyl acetate were added. The aqueous layer was extracted with ethyl acetate (200 mL×2). The combined organic extracts were dried over anhydrous magnesium sulfate, filtered and the filtrate was concentrated under reduced pressure to obtain the title compound 2'-methoxy-3'-nitro-biphenyl-3-carboxylic acid 1d (53.93 g) as a light yellow solid.

MS m/z (ESI): 272 [M−1]

$^1$H NMR (400 MHz, CDCl$_3$): δ 8.11 (s, 1H), 8.02 (d, J=8.0 Hz, 1H), 7.90-7.92 (m, 1H), 7.82-7.84 (m, 1H), 7.21-7.75 (m, 1H), 7.63-7.67 (m, 1H), 7.42-7.46 (m, 1H), 3.45 (s, 3H)

Step 4

2'-Methoxy-3'-amino-biphenyl-3-carboxylic acid

2'-Methoxy-3'-nitro-biphenyl-3-carboxylic acid 1d (0.48 g, 1.74 mmol) was dissolved in 60 mL of ethanol followed by addition of 0.5 g of palladium on carbon (10%) and ammonium formate (1.1 g, 17.4 mmol). The reaction mixture was heated to reflux at 80° C. for 20 minutes. The mixture was filtered and the filtrate was concentrated under reduced pressure and dried to obtain the title compound 2'-methoxy-3'-amino-biphenyl-3-carboxylic acid 1e (0.42 g, yield 93.3%) as a white solid.

MS m/z (ESI): 242 [M−1]

Step 5

3'-Amino-2'-hydroxy-biphenyl-3-carboxylic acid hydrobromide

Employing a known method outlined in patent application WO0189457: 2'-Methoxy-3'-amino-biphenyl-3-carboxylic acid 1e (2.5 g, 10.3 mmol) was dissolved in 100 mL of hydrobromic acid (40%). The reaction mixture was heated to reflux at 120° C. overnight. The mixture was concentrated under reduced pressure and the resulting residue was purified by silica gel column chromatography to obtain the title compound 3'-amino-2'-hydroxy-biphenyl-3-carboxylic acid hydrobromide if (2.4 g, 88.8%) as a khaki solid.

MS m/z (ESI): 230 [M+1]

Step 6

Indan-5-yl-hydrazine

Indan-5-ylamine 1g (3.59 g, 27.0 mmol) was dissolved in 20 mL of concentrated hydrochloric acid upon cooling by an ice-water bath and the mixture was stirred for 10 minutes. 10 mL of sodium nitrite solution (1.86 g, 27.0 mmol) was added dropwise and the mixture was stirred for another 15 minutes and used in the following reaction.

Upon cooling by an ice-salt bath, stannous chloride dihydrate (24.4 g, 108.0 mmol) was dissolved in 10 mL of concentrated hydrochloric acid followed by addition of above mentioned spare mixture. The reaction mixture was warmed up to room temperature and reacted for 1.5 hours. Then the mixture was adjusted to pH 9 with 40% sodium hydroxide solution upon cooling by an ice-water bath. The mixture was extracted with 400 mL of ethyl acetate and the combined organic extracts were concentrated under reduced pressure and dried to obtain the title compound indan-5-yl-hydrazine 1h (2.05 g, yield 51.3%) as a rufous solid.

MS m/z (ESI): 149 [M+1]

Step 7

2-Indan-5-yl-5-methyl-2,4-dihydro-pyrazol-3-one

Indan-5-yl-hydrazine 1h (2.05 g, 13.8 mmol) was dissolved in 50 mL of acetic acid followed by addition of ethyl acetoacetate (1.76 mL, 13.8 mmol). The reaction mixture was heated at 100° C. overnight. The mixture was concentrated under reduced pressure and the resulting residue was purified by silica gel column chromatography to obtain the title compound 2-indan-5-yl-5-methyl-2,4-dihydro-pyrazol-3-one 1i (1.84 g, yield 62.3%) as a yellow solid.

MS m/z (ESI): 215 [M+1]

$^1$H NMR (400 MHz, CDCl$_3$): δ 7.69 (s, 1H), 7.60 (d, J=8.0 Hz, 1H), 7.24 (d, J=8 Hz, 1H), 3.44 (s, 2H), 2.90-2.97 (m, 4H), 3.21 (s, 3H), 2.07-2.14 (m, 2H)

Step 8

(Z)-2'-Hydroxy-3'-[N'-(1-indan-5-yl-3-methyl-5-oxo-1,5-dihydro-pyrazol-4-ylidene)-hydrazino]-biphenyl-3-carboxylic acid Upon cooling by an ice-water bath, 3'-amino-2'-hydroxy-biphenyl-3-carboxylic acid hydrobromide 1f (267 mg, 1.16 mmol) was dissolved in 10 mL of 1M hydrochloric acid followed by dropwise addition of 10 mL of sodium nitrite solution (88 mg, 1.28 mmol) and 2-indan-5-yl-5-methyl-2,4-dihydro-pyrazol-3-one 1i (249 mg, 1.16 mmol). The mixture was adjusted to pH 8 with saturated sodium bicarbonate solution, followed by addition of 10 mL of ethanol. The reaction mixture was warmed up to room temperature overnight. The mixture was filtered, dried and recrystallized from methanol to obtain the title compound (Z)-2'-hydroxy-3'-[N'-(1-indan-5-yl-3-methyl-5-carbonyl-1,5-dihydro-pyrazol-4-ylidene)-hydrazino]-biphenyl-3-carboxylic acid 1j (60 mg, yield 11.4%) as a yellow solid.

MS m/z (ESI): 453 [M−1]

$^1$H NMR (400 MHz, DMSO-d$_6$): δ 13.76 (br. s, 1H), 13.03 (br. s, 1H), 9.66 (br.s, 1H), 8.13 (s, 1H), 7.96-7.98 (d, J=8.1 Hz, 1H), 7.60-7.82 (m, 5H), 7.28-7.30 (d, J=8.1 Hz, 1H), 7.13-7.17 (m, 2H), 2.86-2.93 (m, 4H), 2.34 (s, 3H), 2.03-2.10 (m, 2H)

Step 9

(Z)-2'-Hydroxy-3'-[N'-(1-indan-5-yl-3-methyl-5-oxo-1,5-dihydro-pyrazol-4-ylidene)-hydrazino]-biphenyl-3-carboxylic acid bis-(ethanolamine)

(Z)-2'-hydroxy-3'-[N'-(1-indan-5-yl-3-methyl-5-carbonyl-1,5-dihydro-pyrazol-4-ylidene)-hydrazino]-biphenyl-3-carboxylic acid 1j (454 mg, 1.0 mmol) was dissolved in 16 mL of tetrahydrofuran. The reaction mixture was added with ethanolamine (143 mg, 2.35 mmol), and stirred for 3 hours. The mixture was filtered, the filter cake was washed with tetrahydrofuran (2 mL×3), and the solid was dried in vacuo to obtain the title compound (Z)-2'-hydroxy-3'-[N'-(1-indan-5-yl-3-methyl-5-carbonyl-1,5-dihydro-pyrazol-4-ylidene)-hydrazino]-biphenyl-3-carboxylic acid bis-(ethanolamine) 1 (553 mg, yield: 96.0%) as a dark red solid.

MS m/z (ESI): 453 [M−1]

$^1$H NMR (400 MHz, CD$_3$OD): δ 8.13 (s, 1H), 7.92 (d, J=7.6 Hz, 1H), 7.69 (m, 3H), 7.61 (d, J=8.0 Hz, 1H), 7.45 (t, J=7.6 Hz, 1H), 7.25 (d, J=8.0 Hz, 1H), 7.17 (d, J=8.0 Hz, 1H), 6.98 (t, J=8.0 Hz, 1H), 3.65 (t, J=5.2 Hz, 4H), 2.95 (m, 4H), 2.86 (t, J=5.2 Hz, 4H), 2.41 (s, 3H), 2.12 (m, 2H)

Example 2

(Z)-2'-hydroxy-3'-[N'-(1-indan-5-yl-3-methyl-5-oxo-1,5-dihydro-pyrazol-4-ylidene)-hydrazino]-biphenyl-3-carboxylic acid bis-(diethylamine)

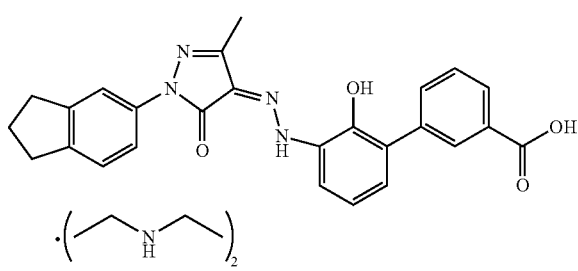

2

(Z)-2'-hydroxy-3'-[N'-(1-indan-5-yl-3-methyl-5-carbonyl-1,5-dihydro-pyrazol-4-ylidene)-hydrazino]-biphenyl-3-carboxylic acid 1j (150 mg, 0.33 mmol) was dissolved in 5 mL of tetrahydrofuran to form a dark red solution. The solution was added dropwise with diethylamine (48 mg, 0.66 mmol) to form a purple solution and stirred for 2 hours. The solid was precipitated from the solution. The mixture was filtered, the filter cake was washed with tetrahydrofuran (1 mL×3), and the solid was dried in vacuo to obtain the title compound (Z)-2'-hydroxy-3'-[N'-(1-indan-5-yl-3-methyl-5-carbonyl-1,5-dihydro-pyrazol-4-ylidene)-hydrazino]-biphenyl-3-carboxylic acid bis-(diethylamine) 2 (132 mg, yield: 66.7%) as a red solid.

HPLC: 99.2%

MS m/z (ESI): 452.9 [M−1]

$^1$H NMR (400 MHz, CD$_3$OD): δ 8.08 (m, 1H), 7.94 (d, J=7.6 Hz, 1H), 7.72 (m, 2H), 7.62 (m, 2H), 7.55 (m, 1H), 7.25 (d, J=8.4 Hz, 1H), 7.14 (d, J=8.4 Hz, 1H), 7.07 (m, 1H), 2.89-2.98 (m, 12H), 2.38 (s, 3H), 2.09-2.14 (m, 2H), 1.34 (m, 12H)

Example 3

(Z)-2'-hydroxy-3'-[N'-(1-indan-5-yl-3-methyl-5-oxo-1,5-dihydro-pyrazol-4-ylidene)-hydrazino]-biphenyl-3-carboxylic acid bis-(piperazine)

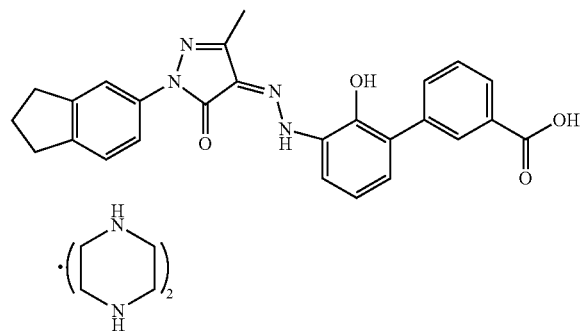

3

(Z)-2'-hydroxy-3'-[N'-(1-indan-5-yl-3-methyl-5-carbonyl-1,5-dihydro-pyrazol-4-ylidene)-hydrazino]-biphenyl-3-carboxylic acid 1j (150 mg, 0.33 mmol) was dissolved in 5 mL of tetrahydrofuran to form a dark red suspension. The reaction mixture was added with piperazine (57 mg, 0.66 mmol) to form a purple solution, and stirred at room temperature for 2 hours. The solid was precipitated from the solution, filtered, then the filter cake was washed with tetrahydrofuran (1 mL×3) and dried in vacuo to obtain the title compound (Z)-2'-hydroxy-3'-[N'-(1-indan-5-yl-3-methyl-5-carbonyl-1,5-dihydro-pyrazol-4-ylidene)-hydrazino]-biphenyl-3-carboxylic acid bis-(piperazine) 3 (130 mg, yield: 62.8%) as a dark red solid.

HPLC: 98.5%

MS m/z (ESI): 452.8 [M−1]

$^1$H NMR (400 MHz, CD$_3$OD): δ 8.10 (s, 1H), 7.92 (d, J=7.6 Hz, 1H), 7.68 (m, 3H), 7.61 (m, 1H), 7.43 (m, 1H), 7.24 (d, J=8.0 Hz, 1H), 7.15 (m, 1H), 7.00 (m, 1H), 2.89-2.95 (m, 4H), 2.84 (s, 16H), 2.39 (s, 3H), 2.09-2.12 (m, 2H)

Example 4

(Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid bis-(ethanolamine)

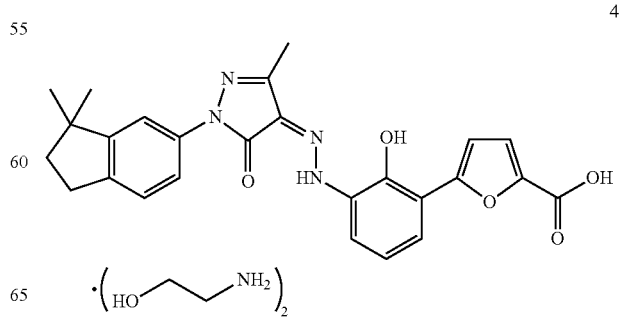

4

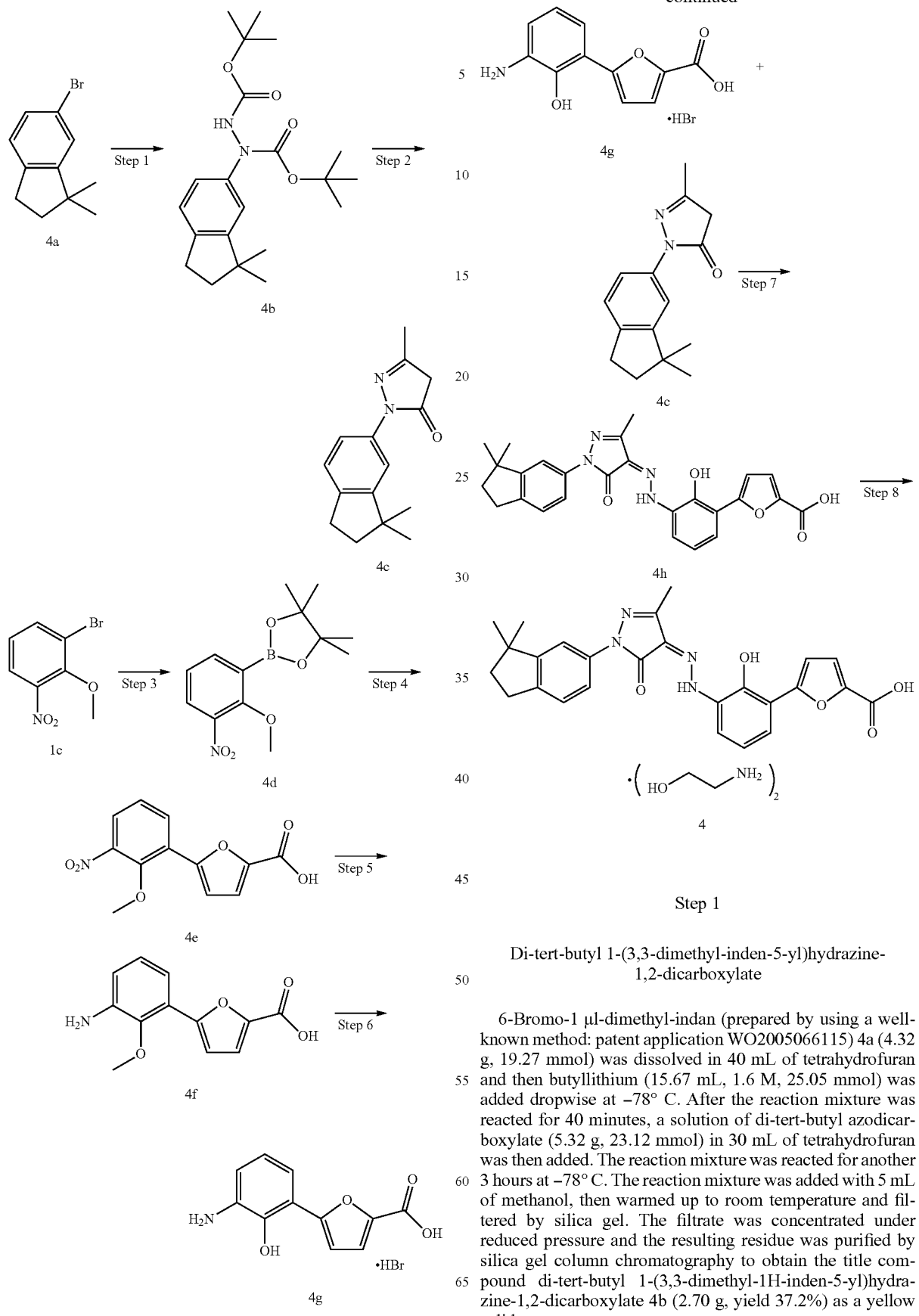

Step 1

Di-tert-butyl 1-(3,3-dimethyl-inden-5-yl)hydrazine-1,2-dicarboxylate

6-Bromo-1 µl-dimethyl-indan (prepared by using a well-known method: patent application WO2005066115) 4a (4.32 g, 19.27 mmol) was dissolved in 40 mL of tetrahydrofuran and then butyllithium (15.67 mL, 1.6 M, 25.05 mmol) was added dropwise at −78° C. After the reaction mixture was reacted for 40 minutes, a solution of di-tert-butyl azodicarboxylate (5.32 g, 23.12 mmol) in 30 mL of tetrahydrofuran was then added. The reaction mixture was reacted for another 3 hours at −78° C. The reaction mixture was added with 5 mL of methanol, then warmed up to room temperature and filtered by silica gel. The filtrate was concentrated under reduced pressure and the resulting residue was purified by silica gel column chromatography to obtain the title compound di-tert-butyl 1-(3,3-dimethyl-1H-inden-5-yl)hydrazine-1,2-dicarboxylate 4b (2.70 g, yield 37.2%) as a yellow solid.

Step 2

2-(3,3-Dimethyl-indan-5-yl)-5-methyl-2,4-dihydro-pyrazol-3-one

Di-tert-butyl 1-(3,3-dimethyl-1H-inden-5-yl)hydrazine-1,2-dicarboxylate 4b (2.70 g, 7.18 mmol) was dissolved in 100 mL of acetic acid followed by addition of 20 mL of trifluoroacetic acid. After the mixture was reacted at room temperature for 2 hours, ethyl acetoacetate (0.98 g, 7.54 mmol) was added. Then the mixture was heated to 100° C. and reacted for 2 hours. The mixture was cooled to room temperature and concentrated under reduced pressure to remove acetic acid. The reaction mixture was neutralized by saturated sodium bicarbonate solution, and then was extracted with ethyl acetate. The combined organic extracts were washed with saturated brine, dried over anhydrous sodium sulfate, filtered and concentrated under reduced pressure. The resulting residue was purified by silica gel column chromatography to obtain the title compound 2-(3,3-dimethyl-indan-5-yl)-5-methyl-2,4-dihydro-pyrazol-3-one 4c (1.0 g, yield 47.7%) as a light brown solid.

MS m/z (ESI): 243 [M+1]

Step 3

2-(2-Methoxy-3-nitro-phenyl)-4,4,5,5-tetramethyl-[1,3,2]dioxaborolane

1-Bromo-2-methoxy-3-nitro-benzene 1c (67 g, 289 mmol), 4,4,4',4',5,5,5',5'-octamethyl-2,2'-bi-1,3,2-dioxaborolane (110 g, 433 mmol), tetrakis(triphenylphosphine)palladium (11.80 g, 14.44 mmol) and potassium acetate (71 g, 724 mmol) were dissolved in 600 mL of etheroxalic acid dimethyl ether. The mixture was heated to reflux for 17 hours. The mixture was concentrated under reduced pressure and the resulting residue was purified by silica gel column chromatography to obtain the title compound 2-(2-methoxy-3-nitro-phenyl)-4,4,5,5-tetramethyl-[1,3,2]dioxaborolane 4d (50.5 g, 61.9%) as a yellow crystal.

Step 4

5-(2-Methoxy-3-nitro-phenyl)furan-2-carboxylic acid

2-(2-Methoxy-3-nitro-phenyl)-4,4,5,5-tetramethyl-[1,3,2]dioxaborolane 4d (10 g, 35.85 mmol), 5-bromofuran-2-carboxylic acid (5.47 g, 28.66 mmol), tetrakis(triphenylphosphine)palladium (2.07 g, 1.79 mmol) and sodium carbonate (7.60 g, 71.66 mmol) were dissolved in the solvent mixture of 200 mL of 1,4-dioxane and 30 mL of water. The reaction mixture was heated to reflux for 2.5 hours. The mixture was filtered and the filtrate was concentrated under reduced pressure. The residue was diluted with 150 mL of water and adjusted to pH 3 with 1 M hydrochloric acid. Then the mixture was filtered and the filter cake was washed with 50 mL of the solvent mixture of n-hexane/ethyl acetate (V/V=1:1). The residue was dried to obtain the title compound 5-(2-methoxy-3-nitro-phenyl) furan-2-carboxylic acid 4e (4.23 g, yield 56.1%) as a grey solid.

MS m/z (ESI): 262 [M−1]

Step 5

5-(3-Amino-2-methoxy-phenyl)-furan-2-carboxylic acid

5-(2-methoxy-3-nitro-phenyl)furan-2-carboxylic acid 4e (4.23 g, 16.09 mmol) was dissolved in 125 mL of ethyl acetate followed by addition of 423 mg of palladium on carbon (10%) and ammonium formate (4.054 g, 64.35 mmol). The reaction mixture was heated to reflux for 3.5 hours. The mixture was concentrated under reduced pressure and the resulting residue was purified by silica gel column chromatography to obtain the title compound 5-(3-amino-2-methoxy-phenyl)-furan-2-carboxylic acid 4f (2.79 g, yield 74.4%) as a light green solid.

MS m/z (ESI): 232 [M−1]

Step 6

5-(3-Amino-2-hydroxy-phenyl)-furan-2-carboxylic acid hydrobromide

5-(3-Amino-2-methoxy-phenyl)-furan-2-carboxylic acid 4f (2.79 g, 11.97 mmol) was dissolved in 25 mL of dichloromethane followed by dropwise addition of boron tribromide (23.9 mL, 2.0 M). The reaction mixture was reacted at room temperature for 1 hour. The mixture was concentrated under reduced pressure after 5 mL of methanol was added. The residue was diluted with 100 mL of ethyl acetate and stirred for 1 hour. Then the mixture was filtered and the filter cake was dried to obtain the title compound 5-(3-amino-2-hydroxy-phenyl)-furan-2-carboxylic acid hydrobromide 4g (1.24 g, yield 47.2%) as a yellow solid.

MS m/z (ESI): 218 [M−1]

Step 7

(Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid

(Z)-5-(3-Amino-2-hydroxy-phenyl)-furan-2-carboxylic acid hydrobromide 4g (333 mg, 1.1 mmol) was dissolved in hydrochloric acid (3.7 mL, 1 M) upon cooling by an ice-water bath, followed by dropwise addition of 1.5 mL of sodium nitrite solution (85 mg, 1.22 mmol). After the mixture was reacted for 20 minutes, 2-(3,3-dimethyl-indan-5-yl)-5-methyl-2,4-dihydro-pyrazol-3-one 4c (242 mg, 1.0 mmol), sodium bicarbonate (1.4 g, 16.67 mmol) and 3 mL of ethanol were added successively. The reaction mixture was reacted overnight at room temperature. The mixture was filtered and 20 mL of water was added to the filter cake. The mixture was adjusted to pH 3-4 with concentrated hydrochloric acid. The mixture was filtered and the filter cake was dried and purified by silica gel column chromatography to obtain the title compound (Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid 4h (190 mg, yield 40.3%) as a red solid.

MS m/z (ESI): 470.9 [M−1]

$^1$H NMR (400 MHz, DMSO-d$_6$): δ 13.74 (br. s, 1H), 13.15 (br. s, 1H), 9.99 (br. s, 1H), 7.71 (m, 3H), 7.55 (d, J=6.8 Hz, 1H), 7.37 (d, J=3.6 Hz, 1H), 7.20 (m, 2H), 7.15 (m, 1H), 2.86 (t, J=7.2 Hz, 2H), 2.33 (s, 3H), 1.92 (t, J=7.2 Hz, 2H), 1.26 (s, 6H)

Step 8

(Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid bis-(ethanolamine)

(Z)-5-(3-{N'-[1-(3,3-dimethyl-indan-5-yl)-3-methyl-5-oxo-1,5-dihydro-pyrazol-4-ylidene]-hydrazino}-2-hydroxyphenyl)-furan-2-carboxylic acid 4h (2.3 g, 4.87 mmol) was dissolved in 20 mL of tetrahydrofuran. The solution was added with ethanolamine (594 mg, 9.75 mmol) and stirred for 1 hour at room temperature. The mixture was filtered, the filter cake was washed with tetrahydrofuran (1 mL×3) and dried in vacuo to obtain the title compound (Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid bis-(ethanolamine) 4 (2.5 g, yield: 86.4%) as a black solid.

MS m/z (ESI): 470.8 [M−1]

$^1$H NMR (400 MHz, CD$_3$OD): δ 7.57 (m, 4H), 7.19 (m, 1H), 7.03 (d, J=3.6 Hz, 1H), 6.95 (d, J=3.6 Hz, 1H), 6.71 (t, J=8.0 Hz, 1H), 3.73 (t, J=5.2 Hz, 4H), 2.98 (m, 4H), 2.88 (t, J=7.2 Hz, 2H), 2.36 (s, 3H), 1.96 (t, J=7.2 Hz, 2H), 1.29 (s, 6H)

Example 5

(Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid bis-(diethylamine)

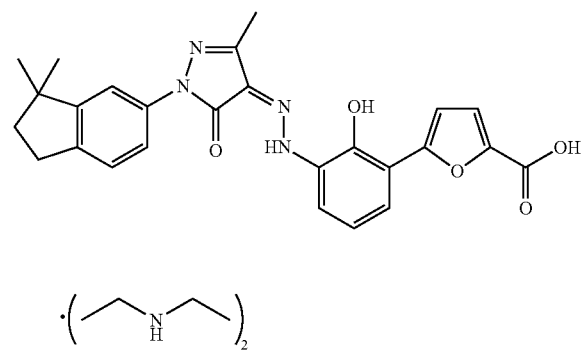

(Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid 4h (150 mg, 0.32 mmol) was dissolved in 5 mL of tetrahydrofuran to form a dark red suspension. The reaction mixture was added with diethylamine (46 mg, 0.63 mmol) to form a purple solution, and stirred at room temperature overnight. The solution was concentrated under reduced pressure, the resulting residue was purified by silica gel column chromatography (hexane:ethyl acetate=10:1), and the solid was dried in vacuo to obtain the title compound (Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid bis-(diethylamine) 5 (170 mg, yield: 86.7%) as a dark red solid.

HPLC: 94.6%

MS m/z (ESI): 471.9 [M−1]

$^1$H NMR (400 MHz, CD$_3$OD): δ 7.60 (m, 4H), 7.19 (m, 1H), 7.04 (m, 1H), 6.87 (m, 2H), 2.98 (q, J=7.2 Hz, 8H), 2.89 (t, J=7.2 Hz, 2H), 2.36 (s, 3H), 1.96 (t, J=7.2 Hz, 2H), 1.27 (t, J=7.2 Hz, 12H), 1.25 (s, 6H)

Example 6

(Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid bis-(piperazine)

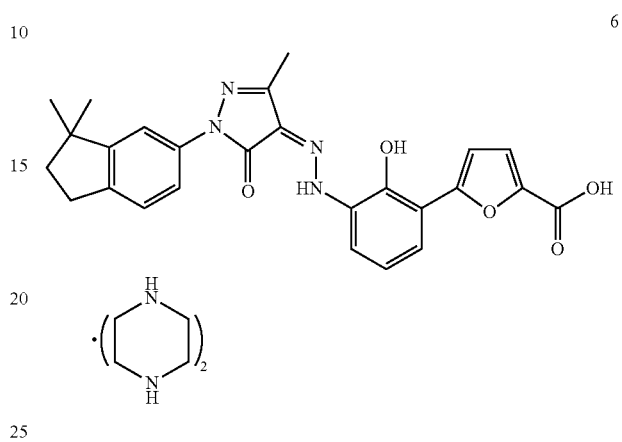

(Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid 4h (150 mg, 0.32 mmol) was dissolved in 5 mL of tetrahydrofuran to form a dark red suspension. The reaction mixture was added with piperazine (55 mg, 0.64 mmol) to form a purple solution, and stirred at room temperature overnight. The mixture was filtered, the filter cake was washed with tetrahydrofuran (1 mL×3), and the solid was dried in vacuo to obtain the title compound (Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid bis-(piperazine) 6 (158 mg, yield: 77.1%) as a red solid.

HPLC: 99.28%

MS m/z (ESI): 471.8 [M−1]

$^1$H NMR (400 MHz, CD$_3$OD): δ 7.64-7.66 (m, 3H), 7.55 (d, J=8.0 Hz, 1H), 7.21 (d, J=8.0 Hz, 1H), 7.04 (m, 1H), 6.87-6.88 (m, 2H), 3.01 (s, 16H), 2.90 (t, J=7.2 Hz, 2H), 2.38 (s, 3H), 1.97 (t, J=7.2 Hz, 2H), 1.29 (s, 6H)

Example 7

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(ethanolamine)

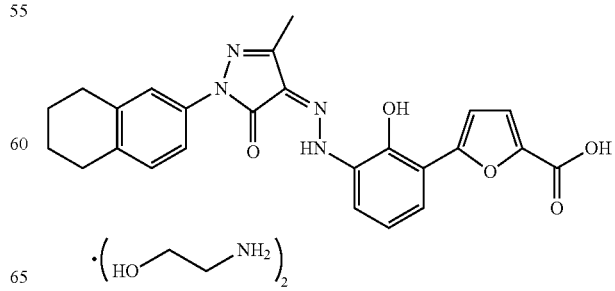

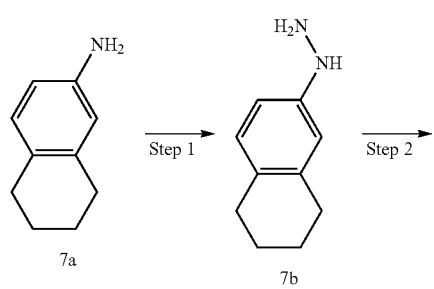

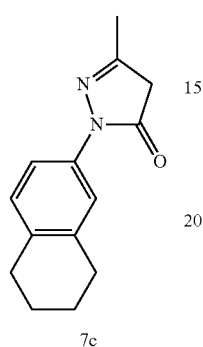

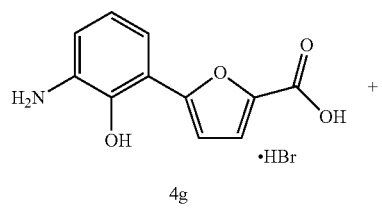

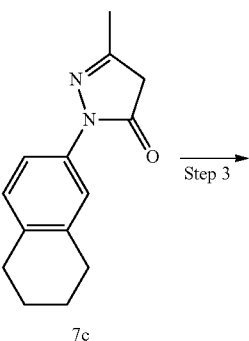

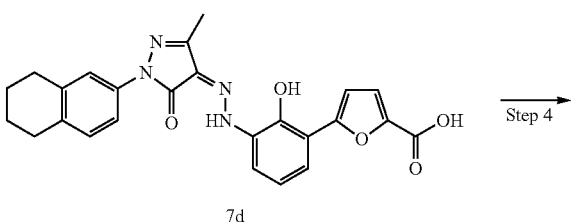

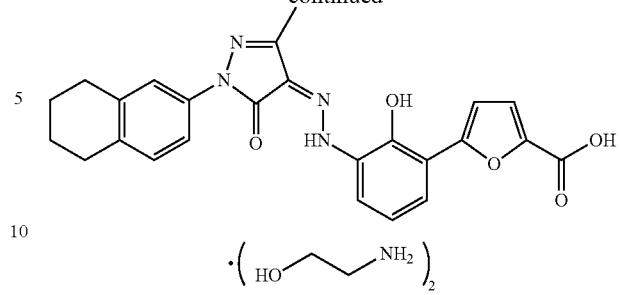

Step 1

(5,6,7,8-Tetrahydro-naphthalen-2-yl)-hydrazine 5,6,7,8-Tetrahydro-naphthalen-2-ylamine 7a (3.68 g, 25.0 mmol) was dissolved in 20 mL of concentrated hydrochloric acid and the mixture was stirred for 10 minutes upon cooling by an ice-water bath. 10 mL of sodium nitrite solution (1.72 g, 25.0 mmol) was added dropwise and the mixture was stirred for another 15 minutes and used in the following reaction.

Upon cooling by an ice-salt bath, stannous chloride dihydrate (22.6 g, 100 mmol) was dissolved in 10 mL of concentrated hydrochloric acid followed by addition of above mentioned spare mixture. The reaction mixture was warmed up to room temperature and reacted for 1.5 hours. Then the mixture was adjusted to pH 9 with 40% sodium hydroxide solution. The mixture was extracted with 400 mL of ethyl acetate, then the combined organic extracts were concentrated under reduced pressure and dried to obtain the title compound (5,6,7,8-tetrahydro-naphthalen-2-yl)-hydrazine 7b (2.19 g, yield 53.7%) as a yellow oil.

MS m/z (ESI): 163 [M+1]

Step 2

5-Methyl-2-(5,6,7,8-tetrahydro-naphthalen-2-yl)-2,4-dihydro-pyrazol-3-one (5,6,7,8-Tetrahydro-naphthalen-2-yl)-hydrazine 7b (2.0 g, 12.3 mmol) was dissolved in 50 mL of acetic acid followed by addition of ethyl acetoacetate (1.57 mL, 12.3 mmol). The reaction mixture was heated to 100° C. overnight. The mixture was concentrated under reduced pressure and the resulting residue was purified by silica gel column chromatography to obtain the title compound 5-methyl-2-(5,6,7,8-tetrahydro-naphthalen-2-yl)-2,4-dihydro-pyrazol-3-one 7c (1.58 g, yield 56.2%) as a colourless oil.

MS m/z (ESI): 457 [2M+1]

$^1$H NMR (CDCl$_3$): δ 7.54-7.58 (m, 2H), 7.09 (d, J=8 Hz, 1H), 3.43 (s, 2H), 2.77-2.81 (m, 4H), 2.21 (s, 3H), 1.80-1.83 (m, 4H).

Step 3

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 5-(3-Amino-2-hydroxy-phenyl)-furan-2-carboxylic acid hydrobromide 4g (292 mg, 0.98 mmol) was dissolved in 3.3 mL of 1M hydrochloric acid upon cooling by an ice-water bath, followed by dropwise addition of 1.3 mL of sodium nitrite solution (74 mg, 1.07 mmol). After the mixture was stirred for 20 minutes, 5-methyl-2-(5,6,7,8-tetrahydro-naphthalen-2-yl)-2,4-dihydro-pyrazol-3-one 7c (200 mg, 0.88 mmol) was added. The mixture was adjusted to pH 8-9 by batch addition of sodium bicarbonate solution (1.226 g, 14.6 mmol). The generated bubbles were quenched with 2 mL of ethanol. The reaction mixture was warmed up to room temperature and reacted overnight. The mixture was filtered and the filter cake was dissolved in 20 mL of water. After mixing well, the mixture was adjusted to pH 3-4 with concentrated hydrochloric acid, filtered and dried. The crude product was purified by HPLC to obtain the title compound (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 7d (160 mg, yield 39.8%) as a red solid.

MS m/z (ESI): 457 [M−1]

¹H NMR (400 MHz, DMSO-d₆): δ 7.71 (d, J=8.4 Hz, 1H), 7.63 (m, 2H), 7.56 (d, J=7.6 Hz, 1H), 7.37 (d, J=3.2 Hz, 1H), 7.22 (t, J=8.0 Hz, 1H), 7.13 (m, 2H), 2.75 (m, 4H), 2.33 (s, 3H), 1.76 (m, 4H)

Step 4

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(ethanolamine)

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 7d (3.3 g, 7.2 mmol) was dissolved in 15 mL of tetrahydrofuran. The reaction solution was added dropwise slowly with ethanolamine (0.88 g, 13 mmol), and stirred for 1.5 hours at 15~20° C. A great quantity of solid was precipitated from the solution, filtered, then the filter cake was washed with tetrahydrofuran (10 mL×3) and dried in vacuo to obtain the title compound (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(ethanolamine) 7 (3g, yield: 74%) as a dark red solid.

HPLC: 99.3%

MS m/z (ESI): 456.8 [M−1]

¹H NMR (400 MHz, CH₃OD): δ7.51 (d, J=8.0 Hz, 1H), 7.44-7.46 (m, 3H), 6.93-6.98 (m, 2H), 6.88 (d, J=3.6 Hz, 1H), 6.67 (t, J=8.0 Hz, 1H), 3.61 (t, J=5.2 Hz, 4H), 2.86 (t, J=5.2 Hz, 4H), 2.65-2.70 (m, 4H), 2.24 (s, 3H), 1.70-1.72 (s, 3H)

Example 8

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(choline)

8

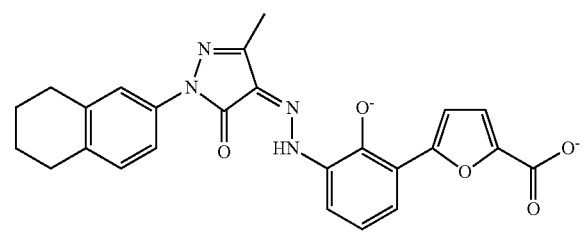

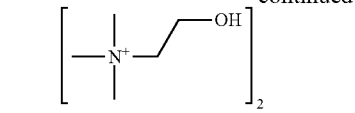

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 7d (100 mg, 0.22 mmol) was dissolved in 5 mL of tetrahydrofuran to form a dark red suspension. The reaction mixture was added with 45% solution of choline hydroxide in methanol (45 mg, 0.44 mmol) to form a purple solution, and stirred for 1 hour at room temperature. The solid was precipitated from solution, filtered, then the filter cake was washed with tetrahydrofuran (1 mL×3) and dried in vacuo to obtain the title compound (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(choline) 8 (140 mg, yield: 96.6%) as a dark red solid.

HPLC: 98.82%

MS m/z (ESI): 457.8 [M−1]

¹H NMR (400M Hz, CD₃OD): δ7.74 (d, J=8.0 Hz, 1H), 7.60 (m, 3H), 7.08 (m, 3H), 6.91 (t, J=8.0 Hz, 1H), 3.96 (m, 4H), 3.45 (t, J=4.8 Hz, 4H), 3.18 (s, 18H), 2.80 (m, 4H), 2.38 (s, 3H), 1.84 (m, 4H)

Example 9

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(diethylamine)

9

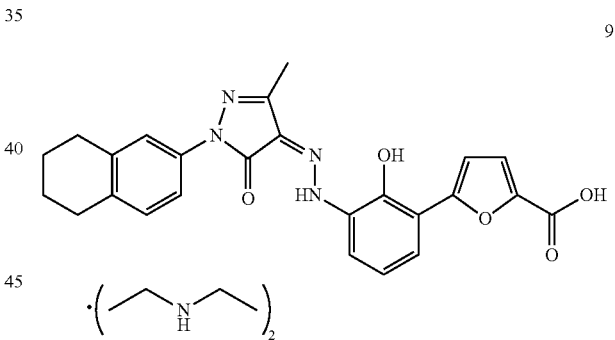

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 7d (100 mg, 0.22 mmol) was dissolved in 5 mL of tetrahydrofuran to form a dark red suspension. The reaction mixture was added dropwise with diethylamine (32 mg, 0.44 mmol) to form a purple solution, and stirred at room temperature overnight. The solid was precipitated from solution, filtered, and the filter cake was washed with tetrahydrofuran (1 mL×3), the solid was dried in vacuo to obtain the title compound (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(diethylamine) 9 (77 mg, yield: 58.3%) as a dark red solid.

HPLC: 99.1%

MS m/z (ESI): 457.9 [M−1]

¹H NMR (400 MHz, CD₃OD): δ 7.59 (m, 4H), 7.08 (d, J=8.0 Hz, 1H), 7.04 (d, J=3.6 Hz, 1H), 6.94 (d, J=3.6 Hz, 1H), 6.82 (t, J=8.0 Hz, 1H), 2.99 (q, J=7.2 Hz, 8H), 2.79 (m, 4H), 2.36 (s, 3H), 1.82 (t, J=3.2 Hz, 4H), 1.27 (t, J=7.2 Hz, 12H)

Example 10

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl-furan-2-carboxylic acid bis-(meglumine)

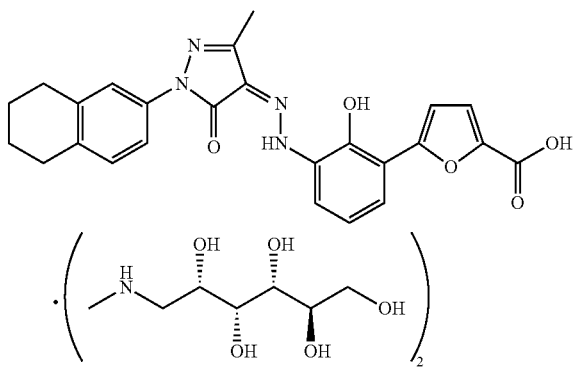

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 7d (100 mg, 0.22 mmol) was suspended in 5 mL of tetrahydrofuran to form a dark red suspension. The reaction mixture was added with meglumine (85 mg, 0.44 mmol), and stirred at room temperature overnight. The resulting solution was added with 4 mL of methanol and concentrated under reduced pressure to obtain the title compound (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(meglumine) 10 (168 mg, yield: 90.8%) as a dark red solid.

HPLC: 97.7%

MS m/z (ESI): 457.8 [M−1]

$^1$H NMR (400 MHz, CD$_3$OD): δ 7.56 (m, 4H), 7.06 (m, 2H), 6.98 (d, J=3.2 Hz, 1H), 6.75 (t, J=7.6 Hz, 1H), 4.08 (m, 2H), 3.81 (m, 2H), 3.77 (m, 2H), 3.63 (m, 6H), 3.11 (m, 4H), 2.76 (m, 4H), 2.64 (s, 6H), 2.33 (s, 3H), 1.79 (m, 4H)

Example 11

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl-furan-2-carboxylic acid bis-(piperazine)

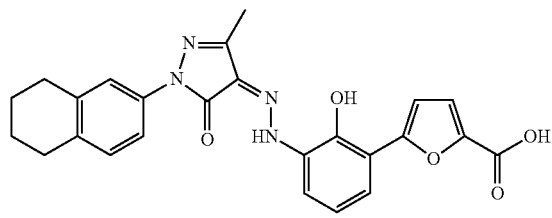

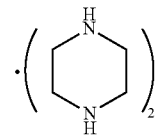

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 7d (100 mg, 0.22 mmol) was dissolved in 5 mL of tetrahydrofuran to form a dark red suspension. The reaction mixture was added with piperazine (37 mg, 0.44 mmol) to form a purple solution, and stirred for 2 hours at room temperature. The solid was precipitated from solution, filtered, then the filter cake was washed with tetrahydrofuran (1 mL×3) and dried in vacuo to obtain the title compound (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(piperazine) 11 (120 mg, yield: 87.6%) as a dark red solid.

HPLC: 98.8%

MS m/z (ESI): 457.8 [M−1]

$^1$H NMR (400 MHz, CD$_3$OD): δ 7.59 (m, 4H), 7.08 (d, J=8.0 Hz, 1H), 7.04 (d, J=3.2 Hz, 1H), 6.87 (d, J=3.2 Hz, 1H), 6.82 (t, J=8.0 Hz, 1H), 3.00 (s, 16H), 2.78 (m, 4H), 2.36 (s, 3H), 1.81 (m, 4H)

Example 12

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl-furan-2-carboxylic acid bis-(trometamol)

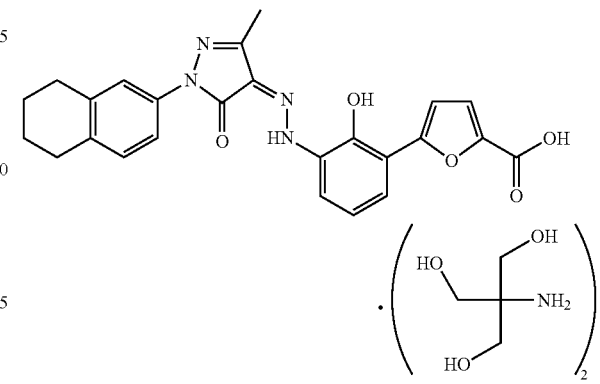

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 7d (100 mg, 0.22 mmol) was dissolved in 5 mL of tetrahydrofuran to form a dark red suspension. The reaction mixture was added with trometamol (53 mg, 0.44 mmol) to form a brown solution, and stirred at room temperature overnight. The solid was precipitated from solution, filtered, then the filter cake was washed with tetrahydrofuran (1 mL×3) and dried in vacuo to obtain the title compound (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(trometamol) 12 (142 mg, yield: 92.8%) as a dark solid.

HPLC: 94.0%

MS m/z (ESI): 457.8 [M−1]

$^1$H NMR (400M Hz, CD$_3$OD): δ 7.58 (m, 4H), 7.05 (m, 2H), 6.96 (d, J=3.6 Hz, 1H), 6.90 (t, J=8.0 Hz, 1H), 3.65 (s, 12H), 2.76 (m, 4H), 2.33 (s, 3H), 1.80 (m, 4H)

Example 13

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(dibenzylethylenediamine)

13

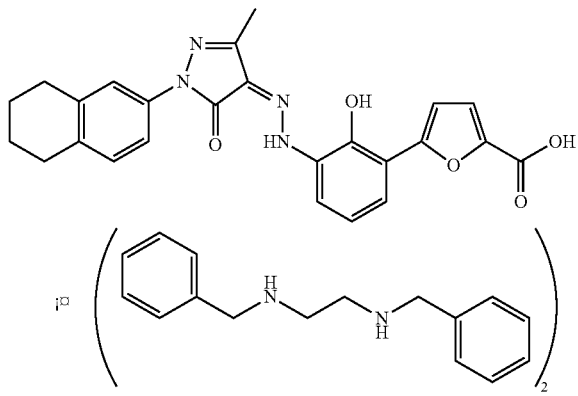

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 7d (100 mg, 0.22 mmol) was dissolved in 5 mL of tetrahydrofuran to form a dark red suspension. The reaction mixture was added with dibenzylethylenediamine (104 mg, 0.44 mmol) to form a brown solution, and stirred for 2 hours at room temperature. The resulting solution was added with 4 mL of methanol and concentrated under reduced pressure to obtain the title compound (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(dibenzylethylenediamine) 13 (167 mg, yield: 81.8%) as a dark solid.

HPLC: 96.8%

MS m/z (ESI): 457.8 [M−1]

$^1$H NMR (400 MHz, CD$_3$OD): δ7.52-7.54 (m, 3H), 7.39 (d, J=7.2 Hz, 1H), 7.24-7.28 (m, 20H), 7.01-7.04 (m, 2H), 6.65-6.72 (m, 1H), 3.89 (s, 8H), 3.01 (s, 8H), 2.73 (m, 4H), 2.32 (s, 3H), 1.78 (m, 4H)

Example 14

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid disodium salt

14

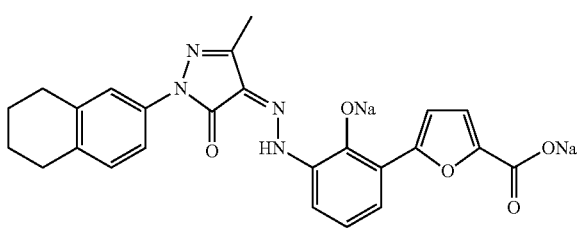

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 7d (110 mg, 0.24 mmol) was dissolved in 4 mL of tetrahydrofuran to form a dark red suspension. The reaction mixture was added dropwise with 1 M sodium hydroxide solution (0.4 mL, 0.44 mmol), stirred for 2 hours at room temperature. The reaction mixture was filtered, then the filtrate was added with 4 mL methanol and concentrated under reduced pressure. The resulting solid was washed with hexane to obtain the title compound (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid disodium salt 14 (115 mg, yield: 81.8%) as a dark solid.

HPLC: 96.8%

MS m/z (ESI): 457.8 [M−1]

$^1$H NMR (400 MHz, CD$_3$OD): δ 7.79 (dd, J$_1$=7.6 Hz, J$_2$=1.2 Hz, 1H), 7.52 (m, 3H), 7.18 (d, J=3.6 Hz, 1H), 7.05 (m, 2H), 6.70 (m, 1H), 2.78 (m, 4H), 2.41 (s, 3H), 1.82 (m, 4H)

Example 15

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(L-arginine)

15

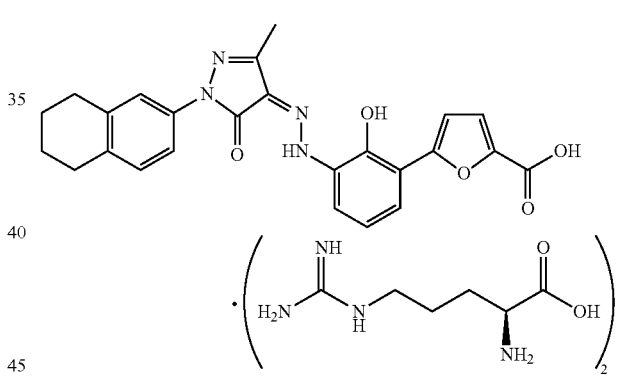

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid 7d (100 mg, 0.22 mmol) was dissolved in 5 mL 1 of tetrahydrofuran to form a dark red suspension The reaction mixture was added with L-arginine (76 mg, 0.44 mmol) and 2 mL of water, stirred for 2 hours at room temperature. The reaction solution was concentrated under reduced pressure, added with 5 mL of ethyl acetate. The solid was precipitated from the solution, filtered, then the filter cake was dried in vacuo to obtain the title compound (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid bis-(L-arginine) 15 (168 mg, yield: 95.5%) as a dark solid.

HPLC: 97.5%

MS m/z (ESI): 457.9 [M−1]

$^1$H NMR (400 MHz, CD$_3$OD): δ 7.59 (m, 4H), 7.06 (m, 2H), 6.98 (d, J=3.6 Hz, 1H), 6.92 (t, J=8.0 Hz, 1H), 3.57 (t, J=6.4 Hz, 2H), 3.19 (m, 4H), 2.78 (m, 4H), 2.36 (s, 3H), 1.83 (m, 8H), 1.73 (m, 4H)

Example 16

(Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid bis-(ethanolamine)

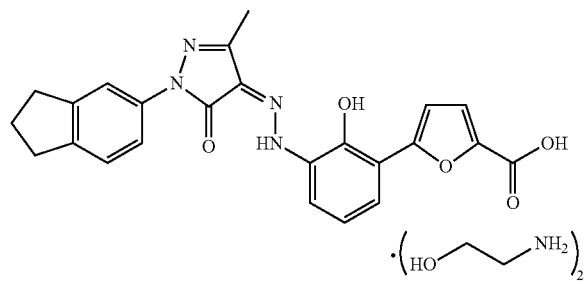

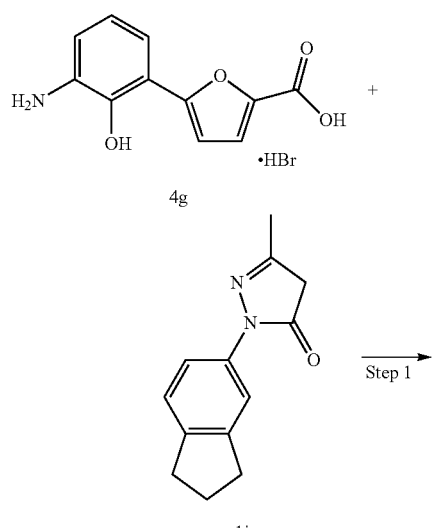

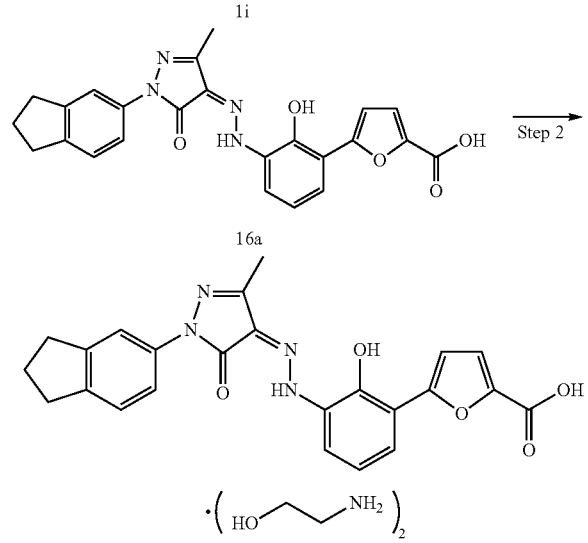

Step 1

(Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid 5-(3-Amino-2-hydroxy-phenyl)-furan-2-carboxylic acid hydrobromide 4g (300 mg, 1.0 mmol) was dissolved in hydrochloric acid (3.4 mL, 1 M) followed by dropwise addition of 1.2 mL of sodium nitrite solution (73 mg, 1.05 mmol) upon cooling by an ice-water bath. After the mixture was reacted for 10 minutes, 2-indan-5-yl-5-methyl-2,4-dihydro-pyrazol-3-one 1i (193 mg, 0.9 mmol), sodium bicarbonate (1.26 g, 15 mmol) and 4.4 mL of ethanol were added successively. The mixture was reacted at room temperature for 24 hours. The mixture was filtered and the filter cake was washed with 20 mL of water and then dissolved in 20 mL of water. Upon cooling by an ice-water bath, the mixture was adjusted to pH<5 with concentrated hydrochloric acid, filtered and dried to obtain the title compound (Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid 16a (287 mg, yield 71.8%) as a yellow solid.

MS m/z (ESI): 443 [M−1]

$^1$H NMR (400 MHz, DMSO-$d_6$): δ 13.73 (br.s, 1H), 9.97 (br. s, 1H), 7.78 (s, 1H), 7.70 (m, 2H), 7.57 (m, 1H), 7.36 (d, J=3.6 Hz, 1H), 7.29 (d, J=8.0 Hz, 1H), 7.22 (t, J=8.0 Hz, 1H), 7.15 (m, 1H), 2.89 (m, 4H), 2.32 (s, 3H), 2.03 (m, 2H)

Step 2

(Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid bis-(ethanolamine)

(Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid 16a (1.825 g, 4.11 mmol) was dissolved in 20 mL of tetrahydrofuran. The reaction mixture was added with ethanolamine (501 mg, 8.22 mmol), and stirred for 2 hours at room temperature. The solid was precipitated from solution, filtered, then the filter cake was washed with tetrahydrofuran (1 mL×3) and dried in vacuo to obtain the title compound (Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid bis-(ethanolamine) 16 (1.615 g, yield: 69.4%) as a dark red solid.

MS m/z (ESI): 443 [M−1]

$^1$H NMR (400 MHz, CD$_3$OD): δ 7.67 (s, 1H), 7.53 (m, 3H), 7.21 (d, J=8.0 Hz, 1H), 7.02 (m, 1H), 6.97 (d, J=3.2 Hz, 1H), 6.70 (m, 1H), 3.70 (m, 4H), 2.92 (m, 4H), 2.88 (m, 4H), 2.35 (s, 3H), 2.08 (m, 2H)

Example 17

(Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid bis-(diethylamine)

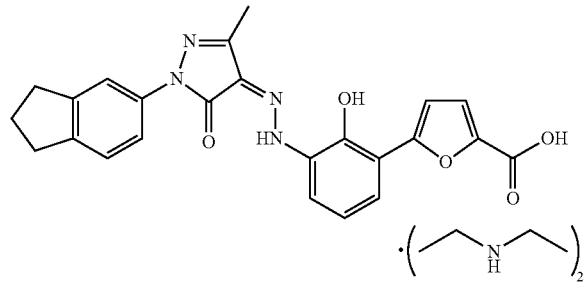

17

(Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid 16a (150 mg, 0.38 mmol) was suspended in 5 mL of tetrahydrofuran to form a dark red suspension. The reaction mixture was added dropwise with diethylamine (49 mg, 0.67 mmol) to form a purple solution, and stirred for 2 hours at room temperature. The solid was precipitated from solution, filtered, then the filter cake was washed with tetrahydrofuran (1 mL×3) and dried in vacuo to obtain the title compound (Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid bis-(diethylamine) 17 (163 mg, yield: 81.9%) as a dark red solid.

HPLC: 99.18%

MS m/z (ESI): 442.7 [M-1]

$^1$H NMR (400 MHz, CD$_3$OD): δ 7.71 (s, 1H), 7.60 (m, 3H), 7.24 (d, J=8.0 Hz, 1H), 7.04 (d, J=8.0 Hz, 1H), 6.95 (d, J=8.0 Hz, 1H), 6.82 (m, 1H), 3.73 (m, 2H), 2.95 (m, 8H), 2.37 (s, 3H), 2.13 (m, 2H), 1.87 (m, 2H), 1.28 (m, 12H)

Example 18

(Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid bis-(piperazine)

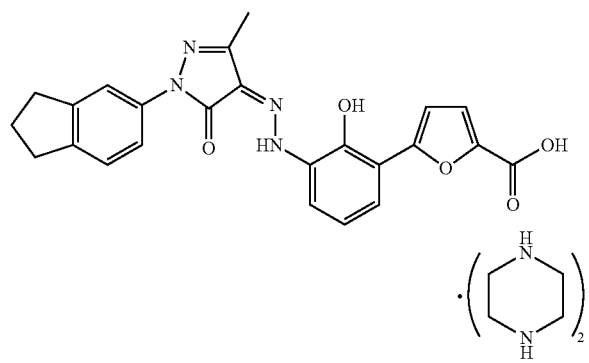

18

(Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid 16a (150 mg, 0.38 mmol) was dissolved in 5 mL of tetrahydrofuran to form a dark red suspension. The reaction mixture was added with piperazine (58 mg, 0.68 mmol) to form a purple solution, and stirred for 3 hours at room temperature. The solid was precipitated from solution, filtered, then the filter cake was washed with tetrahydrofuran (1 mL×3) and dried in vacuo to obtain the title compound (Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid bis-(piperazine) 18 (185 mg, yield: 88.9%) as a dark red solid.

HPLC: 96.52%

MS m/z (ESI): 443.2 [M-1]

$^1$H NMR (400 MHz, CD$_3$OD): δ7.73 (s, 1H), 7.61-7.64 (m, 2H), 7.55 (d, J=8.4 Hz, 1H), 7.23 (d, J=8.4 Hz, 1H), 7.05 (d, J=8.8 Hz, 1H), 6.78-6.90 (m, 2H), 3.03 (s, 16H), 2.89-2.95 (m, 4H), 2.35 (s, 3H), 2.12 (t, J=7.2 Hz, 4H)

Example 19

(Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid bis-(ethanolamine)

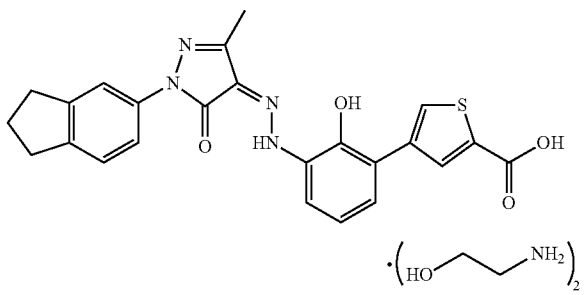

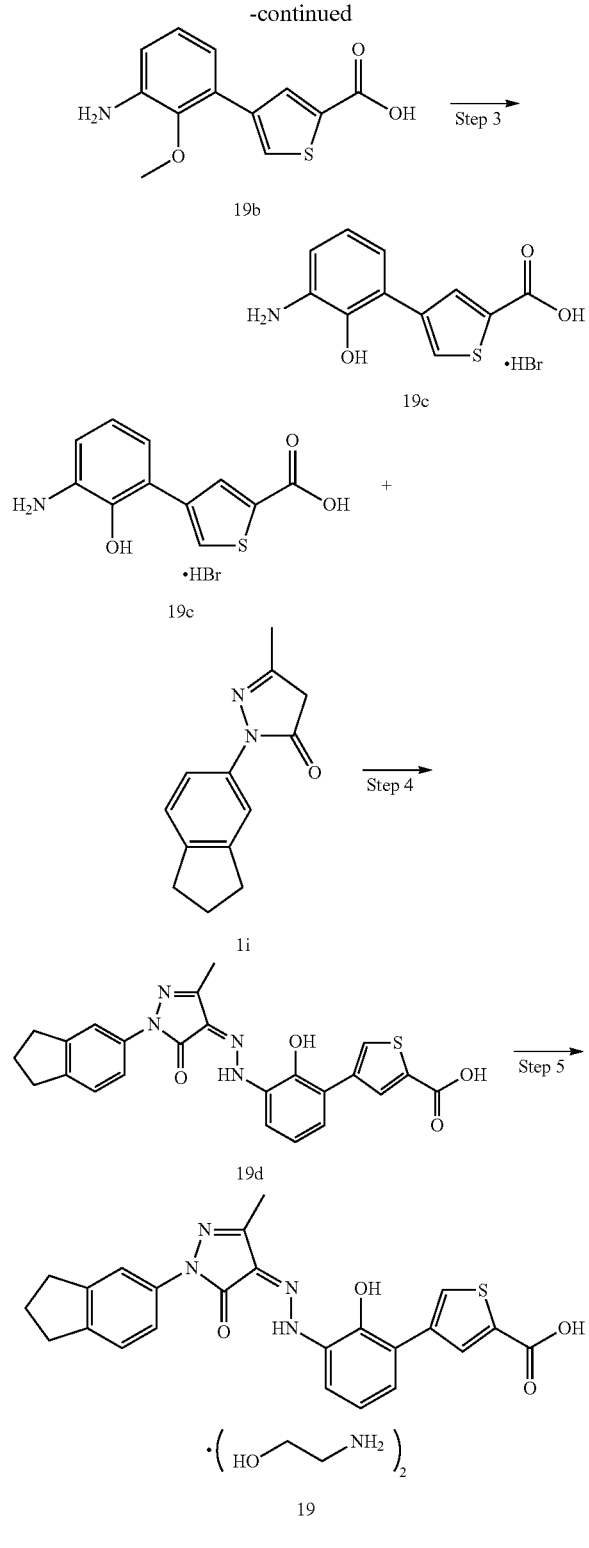

carboxylic acid (0.3 g, 1.45 mmol), tetrakis(triphenylphosphine)palladium (80 mg, 0.073 mmol) and sodium carbonate (0.31 g, 2.9 mmol) were dissolved in a solvent mixture of 20 mL of 1,4-dioxane and 10 mL of water. The reaction was heated to reflux for 0.5 hours. The mixture was adjusted to pH 3 with 1 N hydrochloric acid and extracted with ethyl acetate (20 mL×3). The combined organic extracts were concentrated under reduced pressure and the residue was purified by silica gel column chromatography to obtain the title compound 4-(3-nitro-2-methoxy-phenyl)-thiophene-2-carboxylic acid 19a (0.54 g) as a brown oil, which was directly used in the next step.

MS m/z (ESI): 277.6 [M−1]

Step 2

4-(3-Amino-2-methoxy-phenyl)-thiophene-2-carboxylic acid 4-(3-Nitro-2-methoxy-phenyl)-thiophene-2-carboxylic acid 19a (400 mg, 1.45 mmol) was dissolved in 30 mL of ethyl acetate followed by addition of 100 mg of palladium on carbon (10%) and ammonium formate (360 mg, 5.8 mmol). The mixture was heated to reflux for 3 hours. The mixture was filtered and concentrated under reduced pressure to obtain the title compound 4-(3-amino-2-methoxy-phenyl)-thiophene-2-carboxylic acid 19b (410 mg) as a brown oil, which was directly used in the next step.

MS m/z (ESI): 247.8 [M−1]

Step 3

4-(3-Amino-2-hydroxy-phenyl)-thiophene-2-carboxylic acid hydrobromide 4-(3-Amino-2-methoxy-phenyl)-thiophene-2-carboxylic acid hydrobromide 19b (360 mg, 1.45 mmol) was dissolved in 5 mL of dichloromethane followed by dropwise addition of boron tribromide (2.8 mL, 5.6 mmol). The reaction mixture was reacted at room temperature for 4.5 hours. The reaction mixture was added with 5 mL of methanol and concentrated under reduced pressure. The residue was diluted with 10 mL of ethyl acetate and stirred for 0.5 hours. The mixture was filtered and the filter cake was dried to obtain the title compound 4-(3-amino-2-hydroxy-phenyl)-thiophene-2-carboxylic acid hydrobromide 19c (80 mg, yield 17.5%) as a grey solid.

MS m/z (ESI): 236.1 [M+1]

Step 4

(Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid 4-(3-Amino-2-hydroxy-phenyl)-thiophene-2-carboxylic acid hydrobromide 19c (120 mg, 0.38 mmol) was dissolved in 2.7 mL of 1 M hydrochloric acid upon cooling by an ice-water bath, followed by dropwise addition of 0.45 mL of sodium nitrite solution (29 mg, 0.42 mmol). After the mixture was reacted for 20 minutes, 2-indan-5-yl-5-methyl-2,4-dihydro-pyrazol-3-one 1i (73 mg, 0.34 mmol) was added. The mixture was adjusted to pH 8 with saturated sodium bicarbonate solution followed by addition of 2 mL of ethanol. The reaction mixture was reacted overnight at room temperature. The mixture was filtered and the filter cake was added to 20 mL of water. The mixture was adjusted to pH 3-4 with concentrated hydrochloric acid and filtered. Then 5 mL of ethyl acetate was added to the filter cake and the mixture was stirred for 1 hour. The mixture was filtered and the filter cake was dried to obtain the title compound (Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid 19d (45 mg, yield 28.7%) as a yellow solid.

MS m/z (ESI): 458.8 [M−1]

$^1$H NMR (400 MHz, DMSO-d$_6$): δ13.79 (br. s, 1H), 9.68 (br. s, 1H), 8.13 (d, J=1.2 Hz, 1H), 8.05 (d, J=1.6 Hz, 1H), 7.78 (s, 1H), 7.67 (m, 2H), 7.32 (m, 2H), 7.13 (t, J=8.0 Hz, 1H), 2.87 (m, 4H), 2.32 (s, 3H), 2.05 (m, 2H)

Step 5

(Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid bis-(ethanolamine)

(Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid 19d (1.3 g, 2.83 mmol) was dissolved in 40 mL of tetrahydrofuran to form a dark red suspension. The reaction mixture was added with ethanolamine (344 mg, 5.65 mmol) to form a purple solution, and stirred for 2 hours at room temperature. A great quantity of solid was precipitated from the solution, filtered, then the filter cake was washed with tetrahydrofuran (1 mL×3) and dried in vacuo to obtain the title compound (Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid bis-(ethanolamine) 19 (1.513 g, yield: 92.0%) as a dark red solid.

HPLC: 98.65%

MS m/z (ESI): 458.7 [M−1]

$^1$H NMR (400 MHz, CD$_3$OD): δ 7.94 (s, 1H), 7.88 (s, 1H), 7.68 (s, 1H), 7.55-7.59 (m, 2H), 7.28-7.30 (m, 1H), 7.22 (d, J=8.4 Hz, 1H), 6.83 (t, J=8.0 Hz, 3H), 3.65-3.68 (m, 4H), 2.88-2.92 (m, 8H), 2.38 (s, 3H), 2.06-2.14 (m, 2H)

Example 20

(Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid bis-(diethylamine)

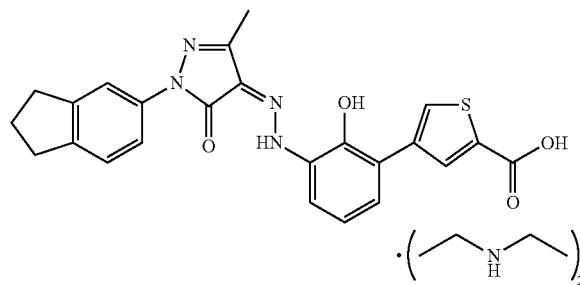

20

(Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid 19d (150 mg, 0.33 mmol) was dissolved in 5 mL of tetrahydrofuran to form a dark red suspension. The reaction mixture was added dropwise with diethylamine (49 mg, 0.66 mmol) to form a purple solution, and stirred for 2 hours at room temperature. The solid was precipitated from solution, filtered, then the filter cake was washed with tetrahydrofuran (1 mL×3) and dried in vacuo to obtain the title compound (Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid bis-(diethylamine) 20 (157 mg, as a dark red solid). yield: 79.3%.

HPLC: 98.98%

MS m/z (ESI): 458.8 [M−1]

$^1$H NMR (400 MHz, CD$_3$OD): δ 7.81 (s, 1H), 7.73 (s, 1H), 7.68-7.70 (m, 2H), 7.62 (d, J=8.8 Hz, 1H), 7.22-7.26 (m, 2H), 7.06 (t, J=8.0 Hz, 1H), 3.03 (q, J=7.2 Hz, 8H), 2.90-2.97 (m, 4H), 2.37 (s, 3H), 2.07-2.15 (m, 2H), 1.29 (t, J=7.2 Hz, 12H)

Example 21

(Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid bis-(piperazine)

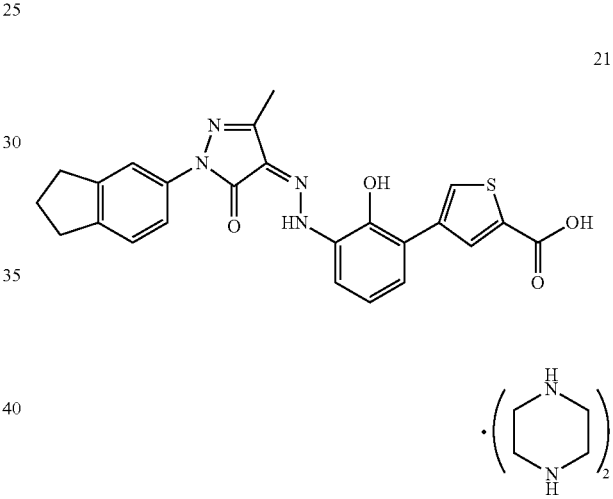

21

(Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid 19d (150 mg, 0.33 mmol) was dissolved in 5 mL of tetrahydrofuran to form a dark red suspension. The reaction mixture was added with piperazine (56 mg, 0.65 mmol) to form a purple solution, and stirred for 2 hours at room temperature. The solid was precipitated from solution, filtered, then the filter cake was washed with tetrahydrofuran (1 mL×3) and dried in vacuo to obtain the title compound (Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid bis-(piperazine) 21 (195 mg, yield: 94.7%) as a dark red solid.

HPLC: 98.17%

MS m/z (ESI): 458.8 [M−1]

$^1$H NMR (400 MHz, CD$_3$OD): δ7.85 (s, 1H), 7.75 (s, 1H), 7.71 (s, 1H), 7.62 (m, 2H), 7.26 (m, 2H), 6.95 (t, 1H), 2.96 (m, 16H), 2.91 (m, 4H), 2.37 (s, 3H), 2.11 (m, 2H)

Example 22

(Z)-4-(2-Hydroxy-3-{N'-[3-methyl-5-oxo-1-(5,6,7,8-tetrahydro-naphthal-2-yl)-1,5-dihydro-pyrazol-4-ylidene]-hydrazino}-phenyl)-furan-2-carboxylic acid bis-(ethanolamine)

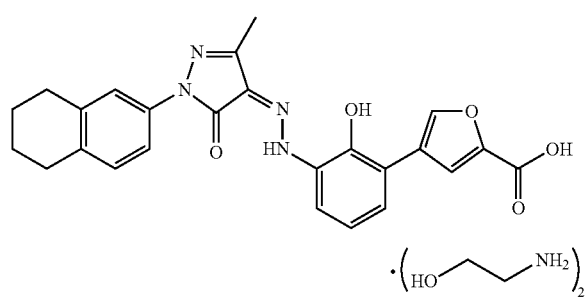

22

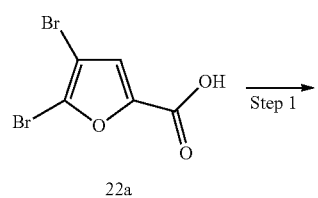

22a

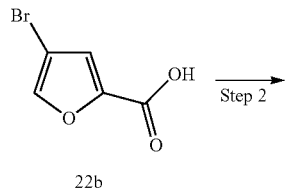

22b

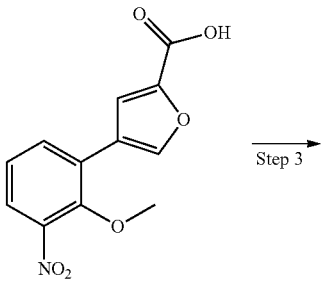

22c

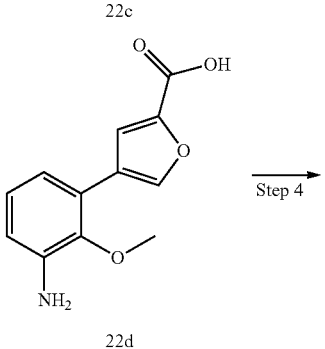

22d

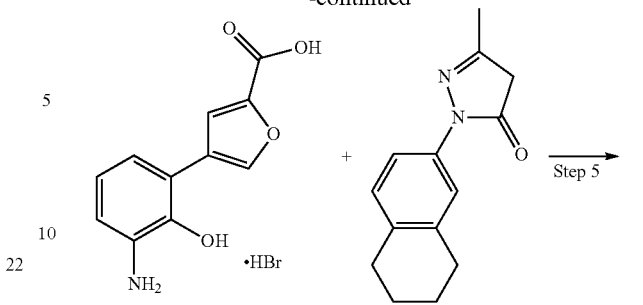

22e  7c

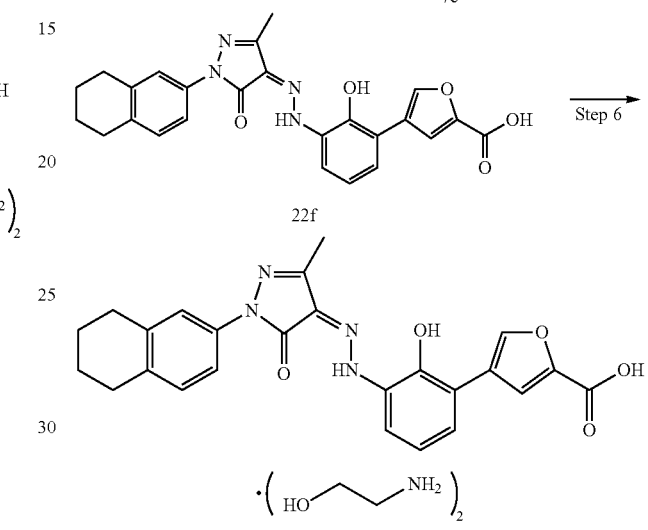

22f

22

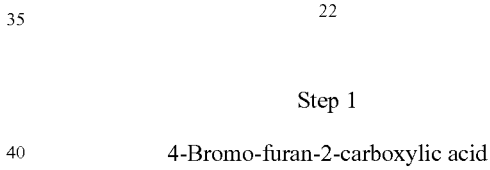

Step 1

4-Bromo-furan-2-carboxylic acid

A mixture of 4,5-dibromo-furan-2-carboxylic acid 22a (5.5 g, 20.3 mmol) and 18 mL of ammonium hydroxide was added to 63 mL of water followed by addition of zinc powder (1.46 g, 22.33 mmol). Upon completion of the addition, the reaction mixture was stirred at room temperature for 6 hours. The mixture was adjusted to pH 3 with 1 M hydrochloric acid to form a great quantity of precipitates. The mixture was filtered and the filter cake was washed with n-hexane (15 mL×4) and dried to obtain the title compound 4-bromo-furan-2-carboxylic acid 22b (3.2 g, yield 83.1%) as a white solid.

MS m/z (ESI): 188.7 [M−1]

Step 2

4-(3-nitro-2-methoxy-phenyl)-furan-2-carboxylic acid 2-(2-Methoxy-3-nitro-phenyl)-4,4,5,5-tetramethyl-1,3,2-dioxaborolane 4d (4 g, 14.34 mmol), 4-bromo-furan-2-carboxylic acid 22b (2.18 g, 11.47 mmol), tetrakis(triphenylphosphine)palladium (829 mg, 0.717 mmol) and potassium carbonate (3.96 g, 28.68 mmol) were dissolved in the solvent mixture of 80 mL of 1,4-dioxane and 30 mL of water. The reaction mixture was heated to reflux for 2.5 hours. The mixture was adjusted to pH 3 with 1 M hydrochloric acid and then extracted with ethyl acetate (80 mL×3). The combined organic extracts were concentrated under reduced pressure. The residue was purified by silica gel column chromatography to obtain the title compound 4-(3-nitro-2-methoxy-phenyl)-furan-2-carboxylic acid 22c (3.42 g, yield 90.7%) as a brown oil.

MS m/z (ESI): 261.8 [M−1]

Step 3

4-(3-Amino-2-methoxy-phenyl)-furan-2-carboxylic acid 4-(3-nitro-2-methoxy-phenyl)-furan-2-carboxylic acid 22c (500 mg, 1.9 mmol) was dissolved in 15 mL of ethyl acetate followed by addition of 100 mg of palladium on carbon and ammonium formate (429 mg, 7.6 mmol). The reaction mixture was heated to reflux for 3 hours. The mixture was filtered to remove palladium on carbon and concentrated under reduced pressure to obtain the title compound 4-(3-amino-2-methoxy-phenyl)-furan-2-carboxylic acid 22d (325 mg, yield 73.4%) as a yellow oil.

MS m/z (ESI): 231.8 [M−1]

Step 4

4-(3-Amino-2-hydroxy-phenyl)-furan-2-carboxylic acid hydrobromide 4-(3-Amino-2-methoxy-phenyl)-furan-2-carboxylic acid 22d (325 mg, 1.4 mmol) was dissolved in 5 mL of dichloromethane followed by dropwise addition of boron tribromide (2.8 mL, 5.6 mmol). The mixture was reacted at room temperature for 4.5 hours. 5 mL of methanol was added and then the mixture was concentrated under reduced pressure. The residue was diluted with 10 mL of ethyl acetate and stirred for 0.5 hours. The mixture was filtered and the filter cake was dried to obtain the title compound 4-(3-amino-2-hydroxy-phenyl)-furan-2-carboxylic acid hydrobromide 22e (174 mg, yield 57.1%) as a grey solid.

MS m/z (ESI): 217.7 [M−1]

Step 5

(Z)-4-(2-Hydroxy-3-{N'-[3-methyl-5-oxo-1-(5,6,7,8-tetrahydro-naphthal-2-yl)-1,5-dihydro-pyrazol-4-ylidene]-hydrazino}-phenyl)-furan-2-carboxylic acid 4-(3-Amino-2-hydroxy-phenyl)-furan-2-carboxylic acid 22e (170 mg, 0.57 mmol) was dissolved in hydrochloric acid (1.9 mL, 1 M) upon cooling by an ice-water bath, followed by dropwise addition of 0.7 mL of sodium nitrite solution (43 mg, 0.63 mmol). After the mixture was reacted for 20 minutes, 5-methyl-2-(5,6,7,8-tetrahydro-naphthalen-2-yl)-2,4-dihydro-pyrazol-3-one 7c (116 mg, 0.51 mmol) was added. The mixture was adjusted to pH 8~9 with saturated sodium bicarbonate solution followed by addition of 2 mL of ethanol. The mixture was reacted at room temperature for 24 hours. The mixture was filtered and then 15 mL of water was added to the filter cake. Upon cooling by an ice-water bath, the mixture was adjusted to pH 2-3 with concentrated hydrochloric acid and filtered. The filter cake was washed with ethyl acetate and dried to obtain the title compound (Z)-4-(2-hydroxy-3-{N'-[3-methyl-5-oxo-1-(5,6,7,8-tetrahydro-naphthal-2-yl)-1,5-dihydro-pyrazol-4-ylidene]-hydrazino}-phenyl)-furan-2-carboxylic acid 22f (13 mg, yield 5.5%) as a red solid.

MS m/z (ESI): 456.7 [M−1]

¹H NMR (400 MHz, DMSO-d₆): δ 13.75 (br. s, 1H), 13.20 (br. s, 1H), 9.68 (br. s, 1H), 8.37 (s, 1H), 7.62-7.68 (m, 4H), 7.41-7.43 (m, 1H), 7.11-7.15 (m, 2H), 2.67-2.76 (m, 2H), 2.31 (s, 3H), 1.75 (m, 4H)

Step 6

(Z)-4-(2-hydroxy-3-{N-[3-methyl-5-oxo-1-(5,6,7,8-tetrahydro-naphthal-2-yl)-1,5-dihydro-pyrazol-4-ylidene]-hydrazino}-phenyl)-furan-2-carboxylic acid bis-(ethanolamine)

(Z)-4-(2-hydroxy-3-{N'-[3-methyl-5-oxo-1-(5,6,7,8-tetrahydro-naphthal-2-yl)-1,5-dihydro-pyrazol-4-ylidene]-hydrazino}-phenyl)-furan-2-carboxylic acid 22f (1.2 g, 2.6 mmol) was dissolved in 20 mL of tetrahydrofuran to form a dark red suspension. The reaction mixture was added with ethanolamine (399 mg, 6.5 mmol) to form a purple solution, and stirred for 6 hours at room temperature. A great quantity of the solid was precipitated from the solution, filtered, then the filter cake was washed with tetrahydrofuran (1 mL×3) and dried in vacuo to obtain the title compound (Z)-4-(2-hydroxy-3-{N'-[3-methyl-5-oxo-1-(5,6,7,8-tetrahydro-naphthal-2-yl)-1,5-dihydro-pyrazol-4-ylidene]-hydrazino}-phenyl)-furan-2-carboxylic acid bis-(ethanolamine) 22 (1.51 g, as a red solid) yield 72.8%.

HPLC: 97.16%

MS m/z (ESI): 456.7 [M−1]

¹H NMR (400 MHz, CD₃OD): δ 8.20 (s, 1H), 7.51-7.56 (m, 3H), 7.31-7.35 (m, 2H), 7.07 (d, J=9.2 Hz, 1H), 6.89 (t, J=8.0 Hz, 1H), 3.68-3.71 (m, 4H), 2.90-2.95 (m, 4H), 2.76-2.81 (m, 4H), 2.39 (s, 3H), 1.80-1.85 (m, 4H)

Example 23

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid choline

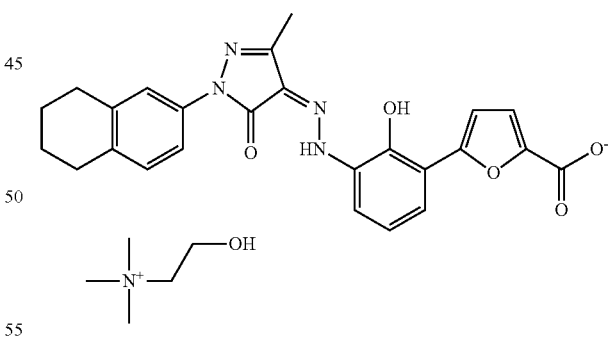

(Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid (1.1 g, 2.4 mmol) was dissolved in 19 mL of the mixture solvent of ethyl acetate and ethanol (V/V=12:7), then the reaction mixture was heated to 40° C., and stirred for 15 minutes to form a marron suspension. The reaction mixture was added slowly with 1 M solution of choline in methanol (2.4 mL, 2.4 mmol) to form a black solution until the solid was disappeared. The reaction solution was added with 1 mL of water, then cooled down to 35° C. and reacted for 3 hours, then stirred for another 72 hours at room temperature. The orange solid was precipitated, filtered, then the filter cake was washed with ethyl acetate (5 mL×3) and dried to obtain the title compound (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid choline (620 mg, yield: 46.0%) as a orange solid.

MS m/z (ESI): 456.7 [M−1]

$^1$H NMR (400 MHz, CD$_3$OD): δ7.66-7.57 (m, 4H), 7.09-7.04 (m, 3H), 6.92 (d, J=3.6 Hz, 1H), 4.03-3.99 (m, 2H), 3.51-3.48 (m, 2H), 3.22 (s, 9H), 2.81-2.75 (m, 4H), 2.33 (s, 3H), 1.83-1.81 (m, 4H)

Example 24

Tablet Composition

Lactose, microcrystalline cellulose, sodium starch glycolate, magnesium stearate and Compound of Example 7 are blended in the proportions shown in Table 1 below. The blend is then compressed into tablets.

TABLE 1

| INGREDIENT | mg |
| --- | --- |
| Compound of Example 7 | 8.45 |
| microcrystalline cellulose | 112 |
| lactose | 70 |
| sodium starch glycolate | 8 |
| magnesium stearate | 2 |

Example 25

Injectable Parenteral Composition

An injectable form for administering Compound of Example 7 is produced by stirring 5.0 mg of the compound in 1.0 mL normal saline.

Test Example

Solubility Assay

According to conventional method for determination of solubility, the solubility of Example compounds and their salts were tested in three different systems: water, 0.1% hydrochloric acid and methanol.

The solubility was characterized by:

The term "very soluble" refers to that 1 g (mL) of solute can be dissolved in less than 1 mL of solvent;

The term "freely soluble" refers to that 1 g (mL) of solute can be dissolved in from 1 mL to 10 mL, not including 10 mL of solvent;

The term "soluble" refers to that 1 g (mL) of solute can be dissolved in from 10 mL to 30 mL, not including 30 mL of solvent;

The term "sparingly soluble" refers to that 1g (mL) of solute can be dissolved in from 30 mL to 100 mL, not including 100 mL of solvent;

The term "slightly soluble" refers to that 1g (mL) of solute can be dissolved in from 100 mL to 1000 mL, not including 1000 mL of solvent;

The term "very slightly soluble" refers to that 1g (mL) of solute can be dissolved in from 1000 mL to 10000 mL, not including 10000 mL of solvent;

The term "practically insoluble or insoluble" refers to that 1g (mL) of solute cannot be dissolved completely in 10000 mL of solvent.

The results of the solubility were shown as follows:

| Example No. | solubility (mg/mL) | | |
| --- | --- | --- | --- |
| | 0.1% hydrochloric acid | water | methanol |
| 1j | <0.001 | <0.001 | <0.001 |
| 1 | <0.001 | 0.003 | 1.469 |
| 3 | <0.001 | 2.290 | 1.534 |
| 4h | <0.001 | <0.001 | <0.001 |
| 4 | 0.024 | 2.905 | 19.001 |
| 6 | <0.001 | 0.001 | 3.009 |
| 7d | <0.001 | <0.001 | <0.001 |
| 7 | 0.029 | 3.960 | 22.377 |
| 8 | <0.001 | 5.049 | 4.595 |
| 9 | <0.001 | 9.974 | 19.331 |
| 10 | <0.001 | 3.715 | 3.417 |
| 11 | <0.001 | 3.003 | 3.617 |
| 12 | <0.001 | 5.945 | 18.823 |
| 13 | <0.001 | <0.001 | 15.432 |
| 14 | <0.001 | 1.876 | 3.722 |
| 15 | <0.001 | 0.645 | 3.023 |
| 16a | <0.001 | <0.001 | <0.001 |
| 17 | <0.001 | 2.000 | 5.849 |
| 18 | <0.001 | 2.741 | 6.096 |
| 19d | <0.001 | <0.001 | <0.001 |
| 20 | <0.001 | 0.068 | 2.221 |
| 21 | <0.001 | 0.814 | 2.416 |
| 23 | <0.001 | 0.286 | 22.597 |

The result showed that comparing to the compound of Example 1j, Example 4h, Example 7d, Example 16a and Example 19d, the solubility of their salts increased obviously, especially in water and methanol. Specially, slats of Example 4 and Example 7 had relatively better solubility in 0.1% hydrochloric acid, and the two salts were very slightly soluble, while the others' were practically insoluble or insoluble.

The structure of Compounds of Example 1j, Example 4h, Example 7d, Example 16a and Example 19d were shown as follows:

| Example No. | Structure | Name |
| --- | --- | --- |
| 1j | 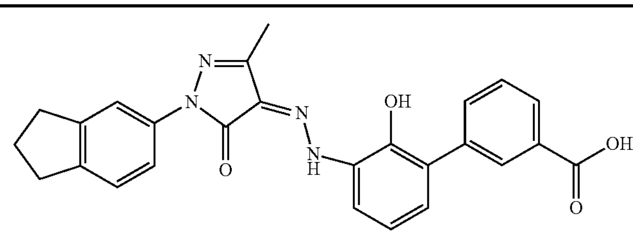 | (Z)-2'-hydroxy-3-[N'-(1-indan-5-yl-3-methyl-5-carbonyl-1,5-dihydro-pyrazol-4-ylidene)-hydrazino]-biphenyl-3-carboxylic acid 1j |

-continued

| Example No. | Structure | Name |
|---|---|---|
| 4h | 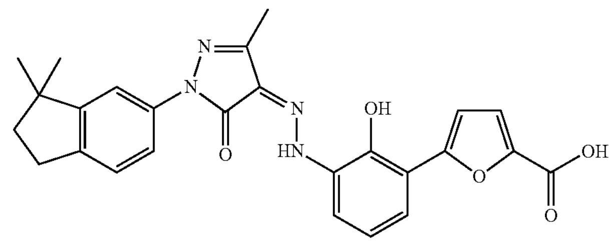 [SMILES: CC1=NN(c2ccc3c(c2)C(C)(C)CC3)C(=O)/C1=N\Nc1cccc(-c2ccc(C(=O)O)o2)c1O] | (Z)-5-(3-{N'-[1-(3,3-dimethyl-indan-5-yl)-3-methyl-5-oxo-1,5-dihydro-pyrazol-4-ylidene]-hydrazino}-2-hydroxy-phenyl)-furan-2-carboxylic acid |
| 7d | 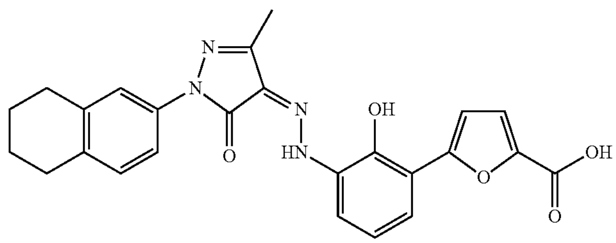 [SMILES: CC1=NN(c2ccc3c(c2)CCCC3)C(=O)/C1=N\Nc1cccc(-c2ccc(C(=O)O)o2)c1O] | (Z)-5-(2-hydroxy-3-{N'-[3-methyl-5-oxo-1-(5,6,7,8-tetrahydro-naphthalen-2-yl)-1,5-dihydro-pyrazol-4-ylidene]-hydrazino}-phenyl)-furan-2-carboxylic acid |
| 16a | 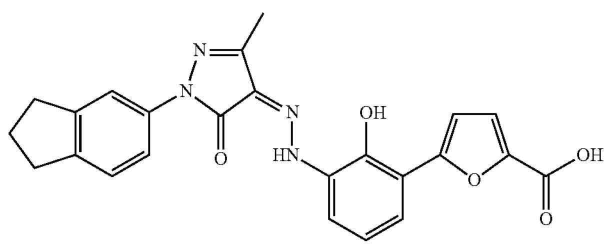 [SMILES: CC1=NN(c2ccc3c(c2)CCC3)C(=O)/C1=N\Nc1cccc(-c2ccc(C(=O)O)o2)c1O] | (Z)-5-{2-hydroxy-3-[N'-(1-indan-5-yl-3-methyl-5-oxo-1,5-dihydro-pyrazol-4-ylidene)-hydrazino]-phenyl}-furan-2-carboxylic acid |
| 19d | 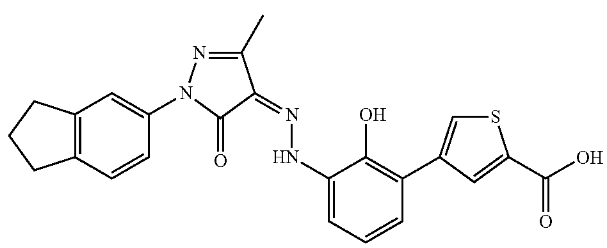 [SMILES: CC1=NN(c2ccc3c(c2)CCC3)C(=O)/C1=N\Nc1cccc(-c2csc(C(=O)O)c2)c1O] | (Z)-4-{2-hydroxy-3-[N'-(1-indan-5-yl-3-methyl-5-oxo-1,5-dihydro-pyrazol-4-ylidene)-hydrazino]-phenyl}-thiophene-2-carboxylic acid |

Hygroscopicity Assay

The hygroscopicity test of the compounds of the present disclosure after standing for 48 hours Protocol:

1. The arid glass weighing bottle with a tap (external diameter is 50 mm, the height is 15 mm) was placed at 25° C.±1° C. suitably in a thermostatic drier (saturated ammonium sulfate solution was laid in the lower part, humidity was 79%) the day before the assay, precise weight was measured as ($m_1$);

2. The above weighing bottle was covered with the compounds of the invention (about 1 g), and the thickness of the compounds were generally 1 mm, precise weight was measured as ($m_2$);

3. The mouth of the weighing bottle was kept open and placed with the tap in the above conditions with constant temperature and humidity for 48 hours;

4. Put the tap back on the bottle, precise weight was measured as ($m_3$)

$$\text{Percentage of weight gain} = \frac{m_3 - m_2}{m_2 - m_1}$$

The degree of hygroscopicity was defined as follows:

Deliquesce: turning into liquid by absorbing enough moisture.

High hygroscopicity: the percentage of hygroscopicity weight gain is not less than 15%.

Hygroscopicity: the percentage of hygroscopicity weight gain is less than 15%, but not less than 2%.

Sparing hygroscopicity: the percentage of hygroscopicity weight gain is less than 2%, but not less than 0.2%.

No hygroscopicity or almost no hygroscopicity: the percentage of hygroscopicity weight gain is less than 0.2%.

The hygroscopicity results of the compounds of the present disclosure were shown as follows:

| Example No. | Percentage of weight gain | hygroscopicity |
|---|---|---|
| 7 | 1.2% | Sparing hygroscopicity |
| 8 | 13.9% | Hygroscopicity |
| 10 | 15.7% | High hygroscopicity |
| 12 | 2.71% | Hygroscopicity |
| 23 | 8.48% | Hygroscopicity |

The results showed that comparing to the other salts, the salt of Example 7, i.e., bis-(ethanolamine) salt of compound 7d, is less hydroscopic, and had better stability in the moisture, which could avoid the potential problems of the weight change of the active components during the preparation of capsules or tables, it is stable in gas, and it is suitable for preparation of conventional formulation and could be stored for long term.

Biological Assay

Test Example 1

Proliferation Effect of a Series of TPO Compounds on BAF3-TPOR Cell

1. Material and Reagents.
   a) RPMI Medium 1640, powder, 10*1 L, containing HEPES (Gibco Catalog No. 23400021).
   b) Fetal Bovine Serum (Gibco Catalog No. 10099-141).
   c) PENICILLIN STREPTOMYCIN SOL (Gibco Catalog No. 15140-122).
   d) Geneticin (G418) (Gibco Catalog No. 11811-098).
   e) Recombinant mouse IL-3 (chemicon Catalog No. IL015).
   f) Human Thrombopoietin R Mab (TPO) (R&D Catalog No. MAB1016).
   g) DMSO, (AppliChem Catalog No. A3672).
   h) QuikChange® Multi Site Directed Mutagenesis Kit, 10 Runs (Stratagene ST200515).
   i) Cell Counting Kit-8 (Dojindo, Catalog No. CK04-13)
   j) BaF3 cell (Union cell culture center, Catalog No. 0095)
   k) EX-EGFP-M02 (FulenGen Catalog No. EX-EGFP-M02 Control)
   l) EX-B0010-M02 (FulenGen Catalog No. EX-B0010-M02)
2. Operating Process:
   (1) Plasmid constructs: based on the TPO receptor (TPOR) sequence information from Entrez (Gene ID: 4325, Refseq: NM_005373), dual-site mutation was performed on EX-B0010-M02 plasmid by using QuikChange® Multi Site Directed Mutagenesis Kit (Stratagene). The sequence of primers containing multi-sites mutation was designed as follows:

```
g491a:
5'-gggaacttcagatcagctgggaggagccg-3' g491a_antisense:
5'-cggctcctcccagctgatctgaagttccc-3';

c965t:
5'-caggaccatgctagctcccaaggcttcttct-3', c965t_antisense:
5'-agaagaagccttgggagctagcatggtcctg-3'.
```

The *E. coli* DH5α competent cells were transformed with mutated plasmid, and positive colonies were picked up through ampicillin selection. The mutation result was confirmed by sequence analysis.

(2) BAF3-TPOR stable transfected cell line: the following method was used to construct the BaF3 cell which stably over-expressed functional human TPOR. The successfully mutated EX-B0010-M02 plasmid (25 ng) which expressed human TPOR and screening gene neomycin was transfected into wild-type BaF3 cells ($1\times10^7$) by electroporation at 250V for 18 ms using an electric pulse generator (Electro Square Porator ECM830, BTX Division of Genetronic, Inc. US). The stable transfected cells BAF3-TPOR were selected with G418 (Gibco, US), then incubated in RPMI1640 medium plus 10% FBS (Gibco, US), 800 ng/mL G418, 5 ng/mL, rmIL-3 (Chemicon, US).

3. Screening Compounds Assay
   (1) Washing cells by centrifugation: a suitable amount of cell suspension was centrifuged at 1000 rpm for 5 minutes, and the supernatant was discarded. 10 mL of cell culture media without IL-3 was added. Then the resulting cell suspension was centrifuged at 1000 rpm for 5 minutes, and the supernatant was discarded.
   (2) 1 mL of cell culture media without IL-3 was added to beat upon them to equality, and the number of a suitable amount of cell suspension was counted after dilution.
   (3) According to the result of the cell counting, a cell suspension in a concentration of 100,000 cell/mL was prepared.
   (4) 100 μL of cell suspension was transferred to each well of 96-well culture plate, and there were 3 parallel wells, that is, there were a blank control group (B), a negative control group (N), a positive control group of TPO (P) and a test compound group (S).
   (5) The test compound was dissolved in DMSO to prepare a 10 mM stock solution, and then the solution was diluted with RPMI 1640 medium into a series of test samples at different concentration: 30 μM, 10 μM, 3 μM, 1 μM, 0.3 μM, 0.1 μM, 0.03 μM, 0.01 μM, 0.003 μM, 0.001 μM.
   (6) 10 μL of test compound solution was transferred to each well respectively; 1 μL of rhTPO (10 ng/mL) was added to positive control well.
   (7) The plates were incubated in an incubator at 5% $CO_2$ and 37° C. for 24 hours.
   (8) After incubation, 10 μL of CCK-8 solution was added to each well and the plates were incubated in the incubator for another 24 hours.
   (9) OD value was detected at 450 nm by VICTORS (Perkin Elmer 1420-120) plate reader.
4. Analytical Calculation
   (1) The proliferation rate was calculated as follows:

Rate=[$(S-B)/(P-B)$]*100%

S: OD value of wells which contain test compound.
   B: OD value of blank control wells
   P: OD value of positive control wells
   (2) The $EC_{50}$ value was calculated by Origin 7.0 software.
5. Results:
   $EC_{50}$ of TPO activity of the compounds of the present disclosure

| Example | $EC_{50}$(nM) |
|---|---|
| Eltrombopag | 299 |
| 1j | 200 |
| 1 | 150 |

-continued

| Example | EC$_{50}$(nM) |
|---------|---------------|
| 4h | 32 |
| 4 | 25 |
| 5 | 19 |
| 6 | 36 |
| 7d | 21 |
| 7 | 19 |
| 8 | 4.4 |
| 9 | 14 |
| 10 | 16 |
| 11 | 21 |
| 12 | 14 |
| 13 | 20 |
| 14 | 19 |
| 15 | 16 |
| 16a | 100 |
| 16 | 18 |
| 17 | 55 |
| 18 | 29 |
| 19d | 43 |
| 19 | 37 |
| 20 | 51 |
| 21 | 116 |
| 22f | 42 |
| 22 | 39 |
| 23 | 43 |

The results of the study showed that comparing to the free acid, the salts of the present disclosure had stronger pro-proliferation effects to BAF3-TPOR cell. The order was as follows: salts of the present disclosure>free acid>Eltrombopag, and the activity of the salts of the present disclosure were more active than Eltrombopag.

Pharmacokinetics Assay

Test Example 1

Pharmacokinetics Assay of the Compounds of the Present Disclosure in Rats

1. Purpose

The compounds of the present disclosure were administrated intragastrically to rats to determine the drug concentration in plasma at different time points by HPLC-UV. The pharmacokinetic behavior of the compounds of the present disclosure was studied and evaluated in rats.

2. Protocol 2.1 Samples

Compounds of Example 1j, Example 1-3, Example 4h, Example 4, Example 5, Example 6, Example 7d, Example 7-15, Example 16a, Example 16-18, Example 19d, Example 19, Example 20, Example 21, Example 22f, Example 22 and Example 23

2.2 Experimental Animals

Healthy adult SD rats, male and female in half, were purchased from SINO-BRITSH SIPPR/BK LAB.ANIMAL LTD., Colo., License number: SCXK (Shanghai) 2003-0002

2.3 Instrument

Waters 2695-2996 high performance liquid chromatograph, Waters Corp., USA;

2.4 Preparation of Test Compounds

The test compound was diluted with 1% sodium carboxymethyl cellulose to 5 mg/mL (calculated as the free acid form) of suspension before use.

2.5 Administration

Healthy adult SD rats, male and female in half, were divided into 23 groups. After an overnight fast, the rats were administered intragastrically at a dose of 50.0 mg/kg (calculated as the free acid form), at a volume of 10 mL/kg.

2.6 Sample Collection

Blood samples (0.2 mL) were taken from eye socket at pre administration and at 0.5, 1.0, 2.0, 3.0, 4.0, 5.0, 6.0, 8.0, 11.0, 14.0, 24.0, 36.0 and 48.0 hours post administration, which were stored in heparinized tubes and centrifuged for 10 minutes at 3,500 rpm. The plasma samples were stored at −20° C. until analysis. The rats were fed 2 hours after administration.

2.7 Analytical Methods

50 μL of rat plasma, obtained at various time points after administration, 50 μL of internal standard solution and 20 μL of a solvent mixture of methanol and water (80:20, v/v) were mixed well, and then 100 μL of methanol was added to result in protein precipitation. Then the mixture was mixed for 3 minute using a vortexer and centrifuged for 10 minutes at 13,500 rpm. 40 μL of the supernatant was analyzed by HPLC-UV.

2.8 Calculation of Pharmacokinetic Parameters

The compartmental model of pharmacokinetics was fitted for the test compounds and the major pharmacokinetic parameters were calculated in which $C_{max}$ and $t_{max}$ were the actually measured values.

3. Results of Pharmacokinetic Parameters

Pharmacokinetic Parameters of the compounds of the present disclosure were shown as follows:

| Pharmacokinetics Assay (50 mg/Kg) | | | | | | | |
|---|---|---|---|---|---|---|---|
| Number | Plasma Conc. Cmax (μg/mL) | Time to peak Tmax (h) | Area Under Curve AUC (μg/mL * h) | Half-Life t½ (h) | Mean Residence Time MRT (h) | Clearance CL/F (l/h/kg) | Apparent Distribution Volume Vz/F (l/kg) |
| Eltrombopag | 61.8 ± 18.7 | 5.5 ± 1.0 | 680 ± 255 | 7.82 ± 1.34 | 11.2 ± 2.6 | 0.089 ± 0.052 | 0.95 ± 0.42 |
| 1j | 29.05 ± 11.44 | 4.00 ± 1.41 | 131 ± 47 | 4.21 ± 1.86 | 3.89 ± 1.78 | 0.049 ± 0.035 | 0.29 ± 0.18 |
| 1 | 90.1 ± 35.3 | 3.25 ± 1.5 | 501 ± 178 | 5.39 ± 0.94 | 4.96 ± 1.16 | 0.098 ± 0.072 | 0.45 ± 0.32 |
| 2 | 83.9 ± 11.2 | 5.0 ± 1.16 | 833 ± 64 | 9.55 ± 1.44 | 11.08 ± 0.76 | 0.06 ± 0.005 | 0.83 ± 0.16 |
| 3 | 79 ± 9.3 | 5.5 ± 1.0 | 842 ± 185 | 8.87 ± 0.78 | 13.0 ± 0.9 | 0.062 ± 0.013 | 0.78 ± 0.15 |
| 4h | 1.29 ± 0.38 | 2.5 ± 1.0 | 9.5 ± 8.3 | 19.8 ± 16.4 | 31.7 ± 24.6 | 3.26 ± 1.93 | 83.4 ± 54.8 |
| 4 | 2.32 ± 1.80 | 2.25 ± 2.47 | 19.0 ± 12.6 | 27.0 ± 31.5 | 38.3 ± 36.5 | 2.42 ± 1.60 | 58.1 ± 47.7 |
| 5 | 19.8 ± 3.8 | 3.25 ± 1.5 | 255 ± 95 | 15.0 ± 6.2 | 20.8 ± 9.1 | 0.22 ± 0.07 | 4.23 ± 0.42 |
| 6 | 13.0 ± 6.5 | 2.5 ± 1.0 | 175 ± 41 | 45.0 ± 70.3 | 60.4 ± 90.2 | 0.30 ± 0.084 | 16.0 ± 22.8 |
| 7d | 16.2 ± 3.9 | 2.5 ± 1.0 | 132 ± 124 | 7.42 ± 7.19 | 11.0 ± 8.13 | 8.14 ± 8.44 | 36.1 ± 17.9 |
| 7 | 74.1 ± 34.5 | 1.75 ± 0.5 | 469 ± 274 | 13.9 ± 6.07 | 13.3 ± 5.72 | 0.175 ± 0.169 | 2.48 ± 0.92 |
| 8 | 36.2 ± 46.2 | 1.38 ± 1.11 | 352 ± 586 | 10.6 ± 9.02 | 12.1 ± 8.23 | 0.926 ± 1.013 | 8.55 ± 9.08 |
| 9 | 21.2 ± 10.4 | 2.88 ± 2.59 | 146 ± 69.7 | 9.65 ± 2.48 | 10.5 ± 1.18 | 0.391 ± 0.145 | 5.15 ± 1.46 |
| 10 | 65.6 ± 44.5 | 1.63 ± 0.75 | 381 ± 306 | 12.9 ± 6.32 | 11.5 ± 5.72 | 0.494 ± 0.754 | 4.54 ± 4.17 |
| 11 | 40.2 ± 24.3 | 1.5 ± 0.58 | 270 ± 178 | 12.1 ± 7.19 | 10.0 ± 3.90 | 0.877 ± 1.465 | 5.80 ± 5.30 |
| 12 | 17.8 ± 10.3 | 1.38 ± 1.11 | 58.5 ± 23.8 | 5.1 ± 2.41 | 5.87 ± 1.68 | 1.00 ± 0.504 | 6.35 ± 1.38 |

Pharmacokinetics Assay (50 mg/Kg)

| Number | Plasma Conc. Cmax (μg/mL) | Time to peak Tmax (h) | Area Under Curve AUC (μg/mL * h) | Half-Life t½ (h) | Mean Residence Time MRT (h) | Clearance CL/F (l/h/kg) | Apparent Distribution Volume Vz/F (l/kg) |
|---|---|---|---|---|---|---|---|
| 13 | 8.10 ± 3.35 | 1.38 ± 1.11 | 42.8 ± 33.2 | 5.70 ± 2.50 | 8.05 ± 2.01 | 1.63 ± 0.83 | 14.9 ± 12.1 |
| 14 | 17.8 ± 22.6 | 5.25 ± 1.5 | 132 ± 189 | 4.72 ± 2.82 | 7.20 ± 2.13 | 2.40 ± 2.41 | 9.54 ± 8.03 |
| 15 | 23.3 ± 13.6 | 2.0 ± 1.16 | 168 ± 118 | 6.56 ± 3.80 | 8.92 ± 2.04 | 0.758 ± 0.995 | 3.65 ± 1.79 |
| 16a | 6.81 ± 6.23 | 2.75 ± 0.96 | 15.0 ± 17.2 | 1.82 ± 0.68 | 4.03 ± 2.55 | 2.98 ± 2.75 | 11.5 ± 7.5 |
| 16 | 19.6 ± 16.3 | 2.00 ± 0.82 | 52.4 ± 48.0 | 2.08 ± 1.74 | 3.84 ± 1.03 | 1.94 ± 0.64 | 6.33 ± 4.57 |
| 17 | 21.5 ± 10.5 | 3.38 ± 3.04 | 138 ± 33 | 12.7 ± 14.7 | 14.0 ± 12.0 | 0.38 ± 0.093 | 8.16 ± 11.09 |
| 18 | 23.3 ± 11.6 | 1.63 ± 1.63 | 119 ± 102 | 3.99 ± 1.60 | 5.31 ± 2.64 | 0.63 ± 0.35 | 3.02 ± 1.01 |
| 19d | 7.91 ± 6.84 | 2.50 ± 0.58 | 36.1 ± 36.4 | 1.84 ± 1.05 | 3.01 ± 1.99 | 1.44 ± 0.83 | 10.4 ± 8.4 |
| 19 | 20.8 ± 17.3 | 1.81 ± 2.79 | 89.2 ± 7.2 | 5.71 ± 3.68 | 7.85 ± 2.92 | 0.88 ± 0.61 | 5.47 ± 2.72 |
| 20 | 46.1 ± 15.7 | 4.5 ± 1.0 | 275 ± 116 | 7.24 ± 2.45 | 7.59 ± 1.33 | 0.21 ± 0.088 | 2.05 ± 0.68 |
| 21 | 61.1 ± 1.38 | 5.5 ± 1.0 | 380 ± 109 | 6.86 ± 0.48 | 8.61 ± 0.31 | 0.14 ± 0.04 | 1.37 ± 0.32 |
| 22f | 8.73 ± 2.58 | 4.25 ± 1.26 | 151 ± 97 | 9.21 ± 1.57 | 11.8 ± 4.5 | 0.69 ± 0.55 | 8.49 ± 2.16 |
| 22 | 39.8 ± 18.2 | 5.0 ± 2.0 | 603 ± 240 | 9.95 ± 0.60 | 14.8 ± 1.0 | 0.24 ± 0.11 | 3.41 ± 1.75 |
| 23 | 17.2 ± 12.3 | 3.25 ± 3.18 | 123 ± 89.5 | 7.61 ± 1.34 | 11.7 ± 1.15 | 0.527 ± 0.24 | 5.52 ± 2.18 |

The results of the study showed that after administration to rats, comparing to the free acid, the pharmacokinetics and bioavailability of the salts of the present disclosure improved obviously. The Pharmacokinetic data of the salt of the Example 7, i.e., the bi-(monoethanlamine) salts of Example 7d, is better, and had good pharmacokinetic characteristics.

Test Example 2

Pharmacokinetics Assay of the Compounds of the Present Disclosure in Beagle Dogs 1. Purpose The compounds of Example 7, Example 8, Example 10 and Example 12 were administrated intragastrically to Beagle dogs to determine the drug concentration in plasma at different time points by HPLC-UV. The pharmacokinetic behavior of the compounds of the present disclosure was studied and evaluated in Beagle dogs.

2. Protocol 2.1 Samples

Compounds of Example 7, Example 8, Example 10 and Example 12

2.2 Experimental Animals

12 Healthy adult Beagles dogs, male, were purchased from Suzhou Xishan Drug Research and Development Colo., LTD. License number: SCXK (Suzhou) 2007-0005.

2.3 Instrument

Agilent 1100 high performance liquid chromatograph, Agilent Corp., USA.

2.4 Preparation of Test Compounds

The test compound was diluted with 0.5% sodium carboxymethyl cellulose to 2.5 mg/mL (calculated as the free acid form) of suspension before use.

2.5. Administration

12 Healthy adult Beagles dogs, male, were divided into 4 groups. After an overnight fast, the dogs were administered intragastrically at a dose of 5.0 mg/kg (calculated as the free acid form), at a volume of 2 mL/kg.

2.6 Sample Collection

Blood samples (1.2 mL) were taken from vein of forelegs at pre administration and at 0.25, 0.5, 1.0, 1.5, 2.0, 3.0, 5.0, 6.0, 8.0, 12.0, 14.0, 24.0 and 48.0 hours post administration, which were stored in heparinized tubes and centrifuged for 10 minutes at 3,500 rpm. The plasma samples were stored at −20° C. until analysis. The Beagles dogs were fed 2 hours after administration.

2.7 Analytical Methods

50 μL of Beagles dog plasma, obtained at various time points after administration, 20 μL of internal standard solution and 150 μL of methanol was added to result in protein precipitation. Then the mixture was mixed for 1 minute using a vortexer and centrifuged for 5 minutes at 11,000 rpm. 50 μL of the supernatant was analyzed by HPLC-UV.

2.8 Calculation of Pharmacokinetic Parameters

The compartmental model of pharmacokinetics was fitted for the test compounds and the major pharmacokinetic parameters were calculated in which $C_{max}$ and $t_{max}$ were the actually measured values.

Pharmacokinetics Assay (5 mg/kg)

| Number | Plasma Conc. $C_{max}$ (μg/mL) | Time to peak $T_{max}$ (h) | Area Under Curve AUC (μg/mL * h) | Half-Life $t_{1/2}$ (h) | Mean Residence Time MRT (h) | Clearance CL/F (L/h/kg) | Apparent Distribution Volume Vz/F (L/kg) |
|---|---|---|---|---|---|---|---|
| 7 | 0.985 | 1.2 | 12.2 | 8.24 | 13.3 | 0.498 | 5.72 |
| 8 | 0.6 | 0.5 | 7.91 | 7.67 | 12.3 | 0.879 | 9.58 |
| 10 | 0.81 | 0.7 | 9.76 | 8.07 | 12.9 | 0.606 | 6.81 |
| 12 | 0.811 | 0.5 | 11.0 | 6.86 | 11.6 | 0.659 | 4.86 |

The data of the four salts in the current study showed that the compounds of Example 7 were obviously superior in pharmacokinetics.

In summary, the preparation of the compounds of the present disclosure was simple and had good yield. Specially, ethanolamine salts, choline salts, diethylamine salts and piperazine salts had superiority in synthesis process because they could crystallize directly. Comparing to free acids, the solubility of salts of the present disclosure increased obviously in conventional solvents. The ethanolamine salts were less hygroscopic and were suitable to prepare conventional formulation and easy to conserve. The bioactivity of the salts of the present disclosure improved obviously. The pharmacokinetics also improved obviously in rats and beagles and had better pharmacokinetic characteristics, especially the ethanolamine salts.

What is claimed is:

1. A method for the treatment of thrombocytopenia comprising administering to a subject in need thereof a therapeutically effective amount of a pharmaceutically acceptable salt of the compound having formula (I):

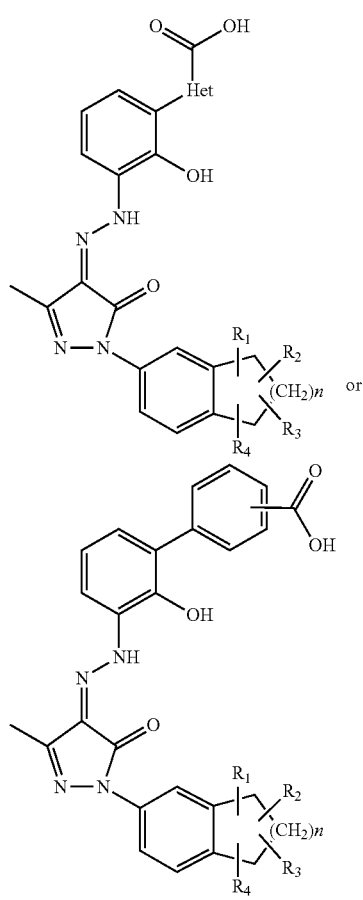

wherein:
Het is selected from the group consisting of furyl and thienyl;
$R_1$, $R_2$, $R_3$ and $R_4$ are each independently selected from the group consisting of hydrogen and alkyl;
n is 0, 1 or 2;
wherein the pharmaceutically acceptable salt is a base addition salt selected from the group consisting of sodium salt, lithium salt, potassium salt, calcium salt, magnesium salt, arginine salt, lysine salt, methanamine salt, dimethylamine salt, trimethylamine salt, ethylamine salt, diethylamine salt, triethylamine salt, ethanolamine salt, piperazine salt, dibenzyl ethylenediamine salt, meglumine salt, tromethamine salt, tetramethyl quaternary ammonium salt, tetraethyl quaternary ammonium salt, choline salt, and combinations thereof.

2. The method according to claim 1, wherein the pharmaceutical salt is co-administered with a drug selected from the group consisting of a colony stimulating factor, a cytokine, a chemokine, an interleukin or cytokine receptor agonist or antagonist, a soluble receptor, a receptor agonist or antagonist antibody, or one or more peptides or small molecule compounds that have the same mechanism as the drug.

3. The method according to claim 1, wherein the pharmaceutical salt is in the form of an oral dosage form.

4. The method according to claim 1, wherein the dosage form is a parenteral dosage form.

5. The method of claim 1, wherein the pharmaceutically acceptable salt of the compound having formula (I) is selected from the group consisting of diethylamine salt, ethanolamine salt, choline salt, piperazine salt, meglumine salt, tromethamine salt, and combinations thereof.

6. The method of claim 1, wherein the pharmaceutically acceptable salt of the compound having formula (I) is selected from the group consisting of ethanolamine salt, choline salt, meglumine salt, tromethamine salt, and combinations thereof.

7. The method of claim 1, wherein the pharmaceutically acceptable salt of the compound having formula (I) is the ethanolamine salt.

8. The method of claim 1, wherein the pharmaceutically acceptable salt of the compound having formula (I) is selected from the group consisting of:

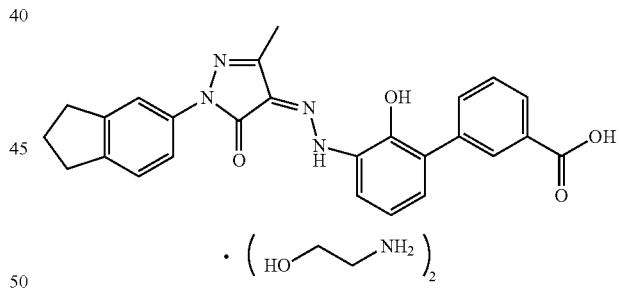

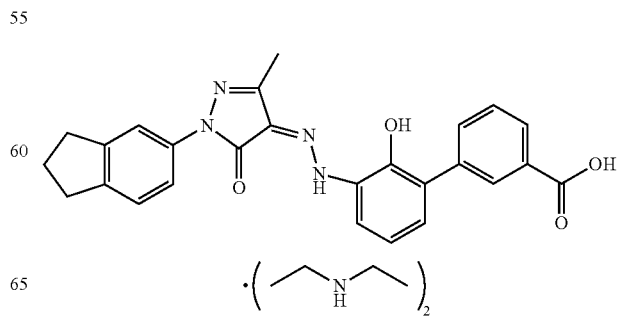

67
-continued
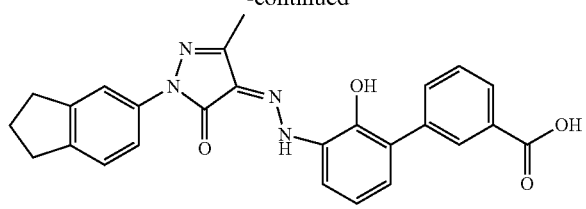
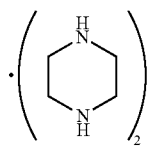
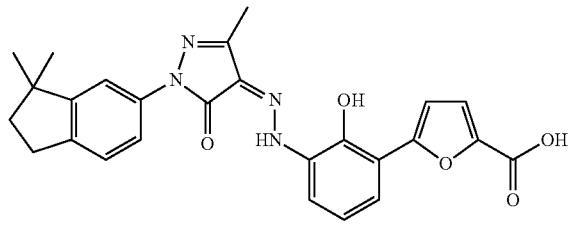
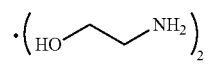
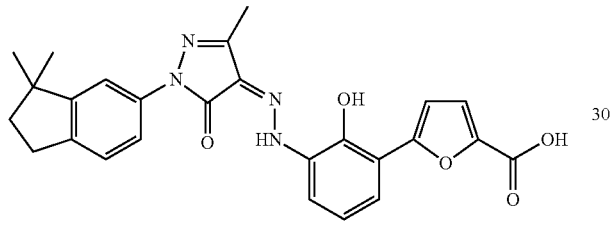
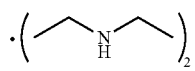
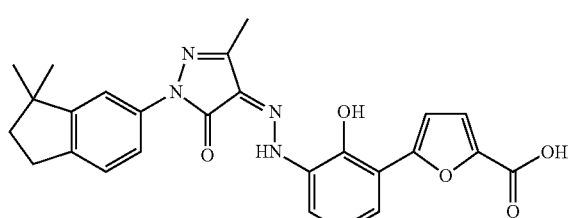
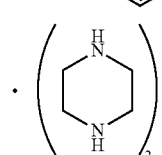
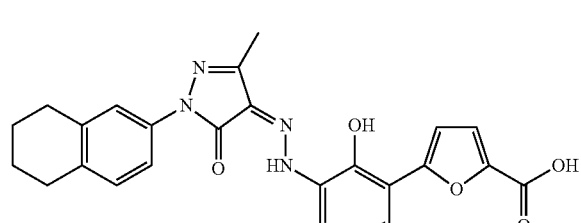
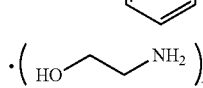
68
-continued
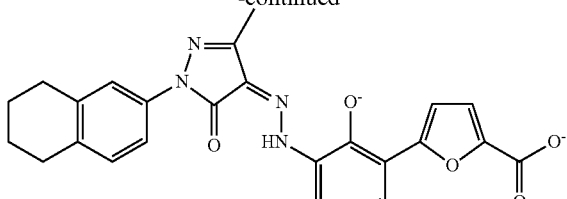
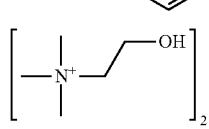
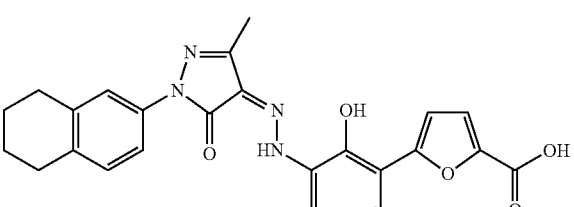
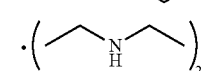
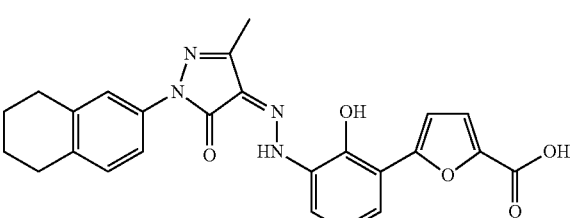
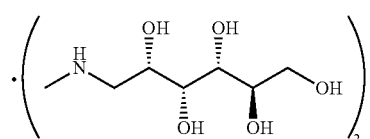
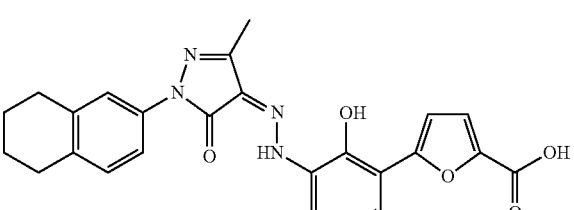
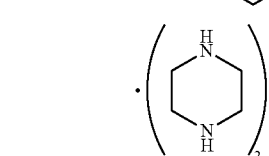

69
-continued
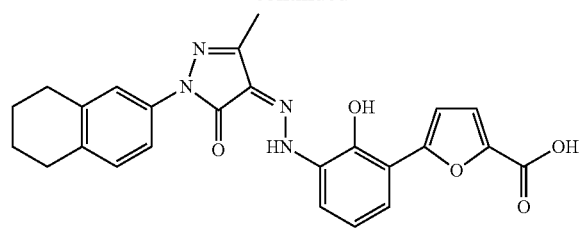
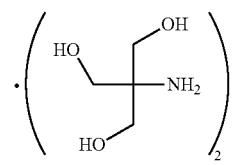
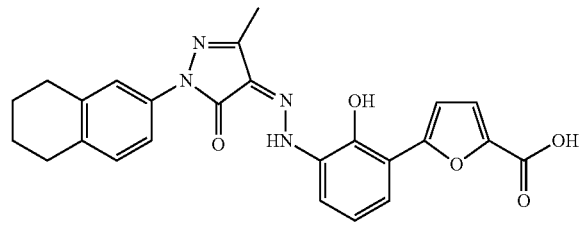
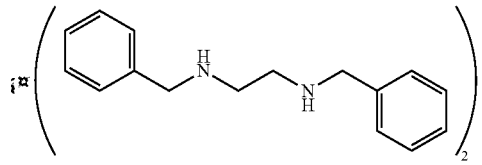
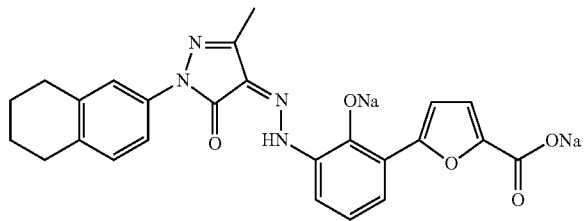
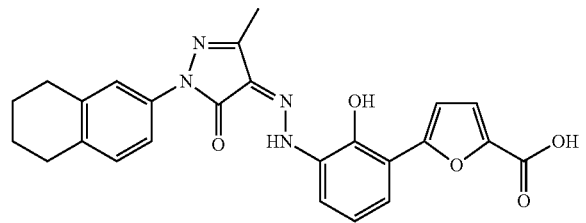
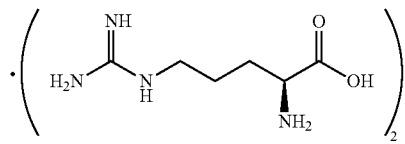
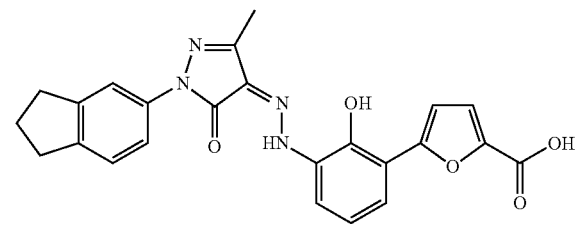
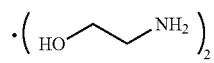
70
-continued
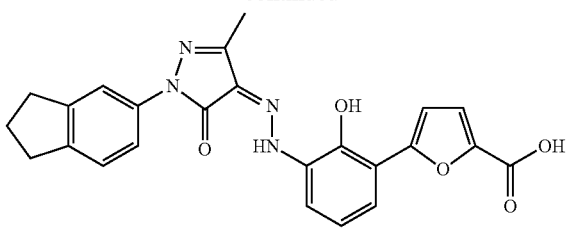
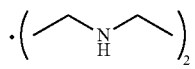
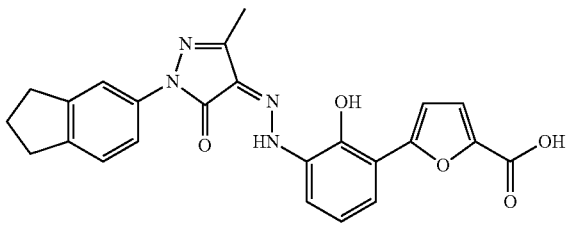
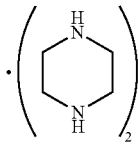
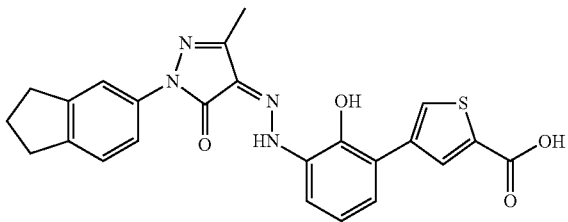
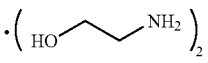
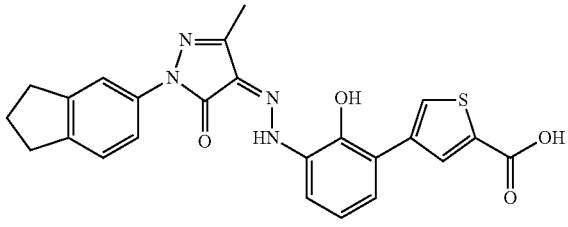
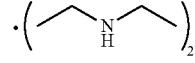
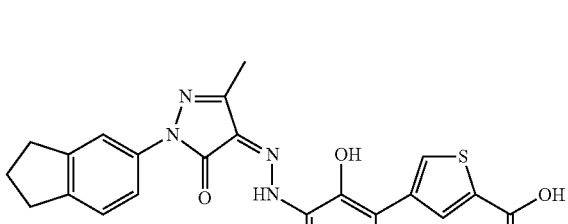
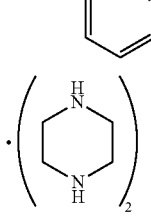

-continued
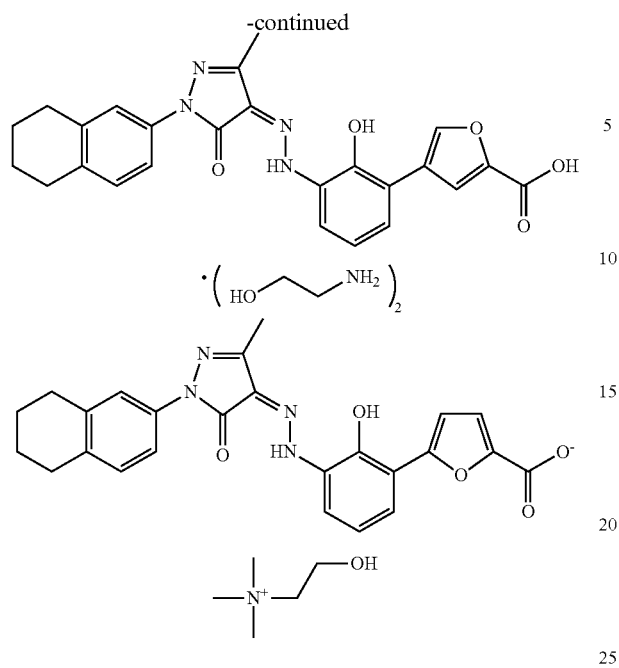
and combinations thereof.
* * * * *